United States Patent [19]
Fuglsang et al.

[11] Patent Number: 5,866,393
[45] Date of Patent: Feb. 2, 1999

[54] **HALOPEROXIDASES FROM *CURVULARIA VERRUCULOSA* AND NUCLEIC ACIDS ENCODING SAME**

[75] Inventors: Claus Fuglsang, Copenhagen; Karen Oxenbøll, Charlottenlund; Torben Halkier, Birkoed, all of Denmark; Randy M. Berka; Joel Cherry, both of Davis, Calif.

[73] Assignees: Novo Nordisk A/S, Bassvaerd, Denmark; Novo Nordisk BioTech, Inc., Davis, Calif.

[21] Appl. No.: 679,405

[22] Filed: Jul. 9, 1996

Related U.S. Application Data

[63] Continuation-in-part of Ser. No. 603,534, Jul. 11, 1996, abandoned.

[60] Provisional application No. 60/001,194 Jul. 14, 1995.

[51] Int. Cl.[6] .............................. C12N 9/08; C12N 15/53
[52] U.S. Cl. ......................... 435/192; 435/911; 536/23.2
[58] Field of Search ..................................... 435/192, 911; 536/23.2

[56] References Cited

U.S. PATENT DOCUMENTS 4,707,446  11/1987  Geigert et al. ........................... 435/132
4,707,447  11/1987  Geigert et al. ........................... 435/132

OTHER PUBLICATIONS

Simons, et al., Eur. J. Biochem, 229, 566–574(1995).

Van Schijndel, et al., Biochim. Biophys. Acta, 1161 (1993) 249–256.

Franssen, et al., Avance In Applied Microbiology, vol. 37, pp. 41–99, XP00069992.

E.G.M. Vollenbroek et al., "Vanadium Chloroperoxidases Occur Widely in Nature", Biochemical Soc. Trans. 23(2): 267–271, 1995.

*Primary Examiner*—Rebecca E. Prouty
*Attorney, Agent, or Firm*—Steve T. Zelson; Elias J. Lambiris

[57] ABSTRACT

The present invention relates to *Curvularia verruculosa* haloperoxidases and isolated nucleic acid fragments comprising nucleic acid sequences encoding the haloperoxidases as well as nucleic acid constructs, vectors, and recombinant host cells comprising the nucleic acid sequences. The invention also relates to methods for recombinant production of the haloperoxidase. The invention further relates to compositions comprising the haloperoxidases and methods of using the compositions for killing microbial cells or inhibiting growth of microbial cells.

24 Claims, 11 Drawing Sheets

```
GAGATGTACATAGTCAGATCTGGCCATCCAACATTTATCCAGTCGGGACACCGGCTCCTTTGCCACCAGTTGGTCACGGAGTTTAAT        90
ATCACATGTGGTTCACGCCAAGCGTGCAATGCGGCTGCTGTGGCTTGTGGCTTGTGGCCTTTGGTTACCGCCTCAGGACAATTTCCATTGACG   180
GCAGTGGTCTGCCACACCGGCTGCAATGCGGCTGTGGGCTTGTGCCTTGCCCCTTGCATGAGAATAGCAGTTCCCGTAACTTTGT           270
GGCTTGACTATGGTTCACCTGATAGCGACGAGTGTACCATTGGAAGAGTCTTCAAGGGTCTTTGAAGGGAACAGAGTGGATGTGTGTGT       360
GTGTGCTACTATCCTTGAAGAATTGACTATAAAGTCTGTGAGCTCTCGCATTCTTTGTTGCAATATCACAATTCATCTACTCATTCTGTG      450
CACCACATATCATCATCACACTACTATGGGGTCCGTTACGATCGATGAACCCGAAGGAGTATAACAACAACT                        540
                  M  G  S  V  T  P  I  P  L  P  T  I  D  E  P  E  E  Y  N  N  N
ACATACTCTTCTGGAATAATGTCGGGCTGGAACTCAACGCCTAACTCACACTGTGGGAGGCCCCTTGACGGGACCGCTCTCTCTGCCA        630
   Y  I  L  F  W  N  N  V  G  L  E  L  N  R  L  T  H  T  V  G  G  P  L  T  G  P  P  L  S  A
GAGCTCTGGGCATGCTGCACTTGGCTATCCACGATGCCTACTTTTCTATCTGTCCTCCTACTGAGTTTACCACCTTTCTCTCCCTGATG       720
   R  A  L  G  M  L  H  L  A  I  H  D  A  Y  F  S  I  C  P  P  T  E  F  T  T  F  L  S  P  D
CTGAGAATCCCGCGTACGGTCTGCCTAGCCCCAATGGGGCAGATGCCCGCAAGCAGTCGCTGGAGCTGCTCTCAAGATGCTGTCTT          810
   A  E  N  P  A  Y  R  L  P  S  P  N  G  A  D  D  A  R  Q  A  V  A  G  A  A  L  K  M  L  S
CGCTATACATGAAGCCTGCCGACCCCAATACCGGCACAACATCTCGACATGCTATGTCGCCCTGGTTCTCGAACGAGCAG              900
   R  Y  T  *  S  L  P  T  P  I  P  A  Q  H  L  D  M  L  C  R  P  G  S  R  T  S  R
S  L  Y  M  K  P  A  D  P  N  T  G  T  N  I  S  D  N  A  Y  A  Q  L  A  L  V  L  E  R  A
TCGTAAAGGTACCGGGGTGGTGTTGATCGAGAGTCAGTCAGCTTCATGTTGGTGAGGCTGTCGCCGATGTCTTCTTTGCACTCCTCAACG      990
   V  K  V  P  G  G  V  D  R  E  S  V  S  F  M  F  G  E  A  V  A  D  V  F  F  A  L  L  N
ATCCTCGAGGTGCTTCACAGAGGGCTACCAGGGCCCCAAGATGCCCCAGGTCGTTATAAATTCGACGATGAGCTACTCACCCAGTGGTAGTCC  1080
   D  P  R  G  A  S  Q  E  G  Y  Q  P  T  P  G  R  Y  K  E  D  D  E  P  T  H  P  V  V  L  V
CCGTAGAGACGGCCAACAACCCCAAGGCCCAAGATGCCCTTTCGCCAGTATCATGACAAGAAGGTTTTGCCA                       1170
   P  V  D  A  N  N  P  N  G  P  K  M  P  F  R  Q  Y  H  A  P  F  Y  G  M  T  I  K  R  F  A
CGGCAGTCCGAGCACATCCTTGCGGACCCAGGATCTCCAGGGCTCCGTTCTAATGGGGATGAGACTGCTGAGTATGACGACTCTATCCGGTGG  1260
   T  Q  S  E  H  I  L  A  D  P  P  G  L  R  S  N  A  D  E  T  A  E  Y  D  D  S  I  R  V  A
TCGGCCCATGGGAGGTGCCAGGATCTCAACTCCACCAACGTAGCCATGGCAGAGCGGCACAGGCCTATACTGGGCCTACGATGGGTCAA     1350
   I  A  M  G  G  A  Q  D  L  N*  S  T  K  R  S  P  W  Q  T  A  Q  G  L  Y  W  A  Y  D  G  S
ACCTTGTTGGAACCCACCCCGGATTCTACAATGCGGATTGTGGTCGACAGTGACTTACAAGAAGATGACCTTGCCAACAGCG             1440
   N  L  V  G  T  P  P  R  F  Y  N  Q  I  V  R  R  I  A  V  T  Y  K  K  E  D  D  L  A  N  S
```

FIG. 10A

```
AAGTCAACAATGCTGATTTTGCCCGCCTCTTCGCCCCTCGTCAACGTCGCTGCTGCACAGAGCGCCGGGCATCTTTTCCTGGAAGGAAAAATGGG 1530
      E  V  N  N  A  D  F  A  R  L  F  A  L  V  N  V  A  C  T  D  A  G  I  F  S  W  K  E  K  W
AGTTTGAATTCTGGCGCCCTTTGTCTGGTGTGAGAGACGATGCCGTCCAGACCACGGAGATCCTTTCTGGCTTACCCTCGGTGCCCCAG 1620
      E  F  F  W  R  P  L  S  G  V  R  D  D  G  R  P  D  H  G  D  P  F  W  L  T  L  G  A  P
CTACAAACACAAACGACATACCCTTCAAGCCTCCTTCCCCGCCTACTGGCCACGCCCATCTGGCGGTGCTGTATTCCAGATGG 1710
      A  T  N  T  D  I  P  F  K  P  P  F  P  A  Y  P  S  G  H  A  T  F  G  G  A  V  F  Q  M
TCCGCCGCTACTACAACGGGGCGTACGCACCTGGAAGGACGAGAACAGAGAACAATTGCCATTGACATGATGATATCGAGGAGCTCA 1800
      V  R  R  Y  Y  N  G  R  V  R  T  W  K  D  D  E  P  D  N  I  A  I  D  M  M  I  S  E  E  L
ACGGCGTGAACCGCGACCTGCGCCAGCCCTACGACCCTGCCCCCATCGAAGACCAACCAGGTATCGTCCGGACCCGCATCGTGCGCC 1890
      N  G  V  N  R  D  L  R  Q  P  Y  D  P  T  A  P  I  E  D  Q  P  G  I  V  R  T  R  I  V  R
ACTTTGACTCAGCTGGGAAATGATGTTCGAAAACGCCATTTCTCGACATCTTCCTGGGCGTCCACTGGCGCTTCGATGCCGCCGCTC 1980
      H  F  D  S  A  W  E  M  M  F  E  N  A  I  S  R  I  F  L  G  V  H  W  R  F  D  A  A  A  A
GGGACATTCTGATCCCCACCAACACAAAGGATGTATGCGTCGACAGCAACGGCGACAGTGTTCCAGAATGTAGAGGATGTCAGGT 2070
      R  D  I  L  I  P  T  N  T  K  D  V  Y  A  V  D  S  N  G  A  T  V  F  Q  N  V  E  D  V  R
ACTCGACCAAGGCACGCGTGAGGGCCGCGTGAGGGCCTCTTCCCTATGGTGGTGCGCTGGGTATCGAGATTGCCGATGAGATTTTA 2160
      Y  S  T  K  G  T  R  E  G  R  E  G  L  F  P  I  G  G  V  P  L  G  I  E  I  A  D  E  I  F
ATAATGGACTTAGGCCCACGCGCCGGAGCTTCAGCCTGGAGCTTCAGCCGCAGGATACCCCGGTGCAGAAGCCGGTTCAGGGCATGTGGGACGAGC 2250
      N  N  G  L  R  P  T  P  P  E  L  Q  P  M  P  Q  D  T  P  V  Q  K  P  V  Q  G  M  W  D  E
AGGTGCGCGTTGGTTAAGGAGGCGCGTAGATGGAGAGGTTTTCGGCAGAGTTACCAGTGACGCTGACGCTGATGGGCGGTGAAGGATGTCTGAT 2340
      Q  V  P  L  V  K  E  A  P  .
TTGGCTGAATGTCTTAATTTGTCAAAATTTGGGGTTTGGTTTAGGATGCTTAGGATGATGCTGCTTGATACTCTGCGATTAATACTCCTATTTGATATTA 2430
CATAAATAGAATGCTTTCGGTAGCTGGAATCTGCTGGTTCACTTATCTTTGTCCCGTTGCATGAGTGGTTGCATGTGAGG 2520
CTCGAATTGATATCTGACCAATTATTGTTCAGTAGGCTTGCTTAAACCTTTTGGTTTCGCAGGAGGATGAAACTGATATATTTGAC 2610
TCAGTAGCTAGACACATAGCAATGAAATGAAAATTAAAAAAAAAAACTCTATCCTTAAAGAAAAATTAAACAAAAAAATCAGGACATATAC 2700
CATGCTCTTTCCAGCTCCAAAACACCTACCACGTTTATCTTCTTGAAACTTCACAATGACAGCACCCACCCCGGCCCCTTCGCCCAC 2790
ATGCAAGCGCCTCCGGGACCCTCCTCAAGCGTC 2822
```

FIG. 10B

```
  1  M G S V T P I P L P K I D E P E E Y N T N Y I L F W N H V G L E L N R V T H T V    C. inaequalis HaP PEP
  1  M G S V T P I P L P ⬚T⬚ I D E P E E Y N ⬚N⬚ N Y I L F W N ⬚N⬚ V G L E L N R ⬚L⬚ T H T V    pAJ014 PEP 41  G G P L T G P P L S A R A L G M L H L A I H D A Y F S I C P P T D F T T F L S P    C. inaequalis HaP PEP
 41  G G P L T G P P L S A R A L G M L H L A I H D A Y F S I C P P T ⬚E⬚ F T T F L S P    pAJ014 PEP 81  D T E N A A Y R L P S P N G A N D A R Q A V A G A A L K M L S S L Y M K P V E Q    C. inaequalis HaP PEP
 81  D ⬚A⬚ E N ⬚P⬚ A Y R L P S P N G A ⬚D⬚ D A R Q A V A G A A L K M L S S L Y M K P ⬚A D —⬚    pAJ014 PEP 121  P N P N P G A N I S D N A Y A Q L G L V L D R S V L E A P G G V D R E S A S F M    C. inaequalis HaP PEP
120  ⬚— —⬚ P N ⬚T⬚ G ⬚I⬚ N I S D N A Y A Q L ⬚A⬚ L V L E ⬚R⬚ ⬚I A⬚ V ⬚K V⬚ P G G V D R E S ⬚V⬚ S F M    pAJ014 PEP 161  F G E D V A D V F F A L L N D P R G A S Q E G Y H P T P G R Y K F D D E P T H P    C. inaequalis HaP PEP
158  F G E ⬚A⬚ V A D V F F A L L N D P R G A S Q E G Y ⬚Q⬚ P T P G R Y K F D D E P T H P    pAJ014 PEP 201  V V L I P V D P N N P N G P K M P F R Q Y H A P F Y G K T T K R F A T Q S E H F    C. inaequalis HaP PEP
198  V V L ⬚V⬚ P ⬚V⬚ D P N N P N G P K M P F R Q Y H A P F Y G ⬚M⬚ T T K R F A T Q S E H ⬚I⬚    pAJ014 PEP 241  L A D P P G L R S N A D E T A E Y D D A V R V A I A M G G A Q A L N S T K R S P    C. inaequalis HaP PEP
238  L A D P P G L R S N A D E T A E Y D D ⬚S⬚ ⬚I⬚ R V A I A M G G A Q ⬚D⬚ L N S T K R S P    pAJ014 PEP 281  W Q T A Q G L Y W A Y D G S N L I G T P P R F Y N Q I V R R I A V T Y K K E E D    C. inaequalis HaP PEP
278  W Q T A Q G L Y W A Y D G S N L ⬚V⬚ G T P P R F Y N Q I V R R I A V T Y K K E ⬚D⬚ D    pAJ014 PEP 321  L A N S E V N N A D F A R L F A L V D V A C T D A G I F S W K E K W E F E F W R    C. inaequalis HaP PEP
318  L A N S E V N N A D F A R L F A L V ⬚N⬚ V A C T D A G I F S W K E K W E F E F W R    pAJ014 PEP
```

FIG. 11A

```
361  P L S G V R D D G R P D H G D P F W L T L G A P A T N Y N D I P F K P P F P A Y    C. inaequalis HaP PEP
358  P L S G V R D D G R P D H G D P F W L T L G A P A T N T N D I P F K P P F P A Y    pAJ014 PEP 401  P S G H A T F G G A V F Q M V R R Y Y N G R V G T W K D D E P D N I A I D M M I    C. inaequalis HaP PEP
398  P S G H A T F G G A V F Q M V R R Y Y N G R V G T W K D D E P D N I A I D M M I    pAJ014 PEP 441  S E E L N G V N R D L R Q P Y D P T A P I E D Q P G I V R T R I V R H F D S A W    C. inaequalis HaP PEP
438  S E E L N G V N R D L R Q P Y D P T A P I E D Q P G I V R T R I V R H F D S A W    pAJ014 PEP 481  E L M F E N A I S R I F L G V H W R F D A A A A R D I L I P T T T K D V Y A V D    C. inaequalis HaP PEP
478  E M M F E N A I S R I F L G V H W R F D A A A A R D I L I P T N K D V Y A V D      pAJ014 PEP 521  N N G A T V F Q N V E D I R Y T T R G T R E D P E G L F P I G G V P L G I E I A    C. inaequalis HaP PEP
518  S N G A T V F Q N V E D V R Y S T K G T R E G R E G L F P I G G V P L G I E I A    pAJ014 PEP 561  D E I F N N G L K P T P P E I Q P M P Q E T P V Q K P V G Q Q P V K G M W E E E    C. inaequalis HaP PEP
558  D E I F N N G L R P T P P E L Q P M P Q D T P V Q K P V - - - - - Q G M W D E -    pAJ014 PEP 601  Q A P V V K E A P                                                                  C. inaequalis HaP PEP
592  Q V P L V K E A P                                                                  pAJ014 PEP
```

FIG.11B

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 2822 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 477..2276

( x i ) SEQUENCE DESCRIPTION: SEQ ID NO:1:

```
GAGATGTACA  TACGTCAGAC  CTGGCCATCC  AACATTTATC  CCAGTCGGAC  ACCGGCTCCT      60

TTCGCCACCA  GTTGGTCACC  GAGTTTTAAT  ATCACATGTG  GTTCACGCCA  AGCGTAAGCA     120

GCCAAACTGA  TCTCCCTAGA  TCCGTCTTGG  TTACCGCCTC  AGGACAATTT  CCATTTGACG     180

GCAGTGGTCT  GCCACACCGC  TGCAATGCGG  CTGTGGCTTC  ACGTCTGCCT  TGCGCCCTTG     240
```

```
CATGAGAATA GCAGTTCCCC GTAACTTTGT GGCTTGACTA TGGTTCACCT GATAGCGACG      300

AGTGTACCAT TCTAAGAGTC TTCAAGGGTC TTTTGAAGGG AACAGAGTGG ATGTGTGTGT      360

GTGTGCTGAT ATCCTTGAAG AATTGACTAT AAAGTCTGTG AGCTCTCGCA TTCTTTGTTG      420

CAATATCACA ATTCATCTAC TCATTCTGTG CACCACATAT CATCATCACA CCTACT         476
```

| | | | | | | | | | | | | | | | | |
|---|---|---|---|---|---|---|---|---|---|---|---|---|---|---|---|---|
| ATG | GGG | TCC | GTT | ACA | CCA | ATT | CCG | TTG | CCT | ACG | ATC | GAT | GAA | CCC | GAA | 524 |
| Met | Gly | Ser | Val | Thr | Pro | Ile | Pro | Leu | Pro | Thr | Ile | Asp | Glu | Pro | Glu | |
| 1 | | | | 5 | | | | | 10 | | | | | 15 | | |
| GAG | TAT | AAC | AAC | AAC | TAC | ATA | CTC | TTC | TGG | AAT | AAT | GTC | GGG | CTG | GAA | 572 |
| Glu | Tyr | Asn | Asn | Asn | Tyr | Ile | Leu | Phe | Trp | Asn | Asn | Val | Gly | Leu | Glu | |
| | | | 20 | | | | | 25 | | | | | 30 | | | |
| CTC | AAC | CGC | CTA | ACT | CAC | ACT | GTG | GGA | GGC | CCC | TTG | ACG | GGA | CCG | CCT | 620 |
| Leu | Asn | Arg | Leu | Thr | His | Thr | Val | Gly | Gly | Pro | Leu | Thr | Gly | Pro | Pro | |
| | | 35 | | | | | 40 | | | | | 45 | | | | |
| CTC | TCT | GCC | AGA | GCT | CTG | GGC | ATG | CTG | CAC | TTG | GCT | ATC | CAC | GAT | GCC | 668 |
| Leu | Ser | Ala | Arg | Ala | Leu | Gly | Met | Leu | His | Leu | Ala | Ile | His | Asp | Ala | |
| | 50 | | | | | 55 | | | | | 60 | | | | | |
| TAC | TTT | TCT | ATC | TGT | CCT | CCT | ACT | GAG | TTT | ACC | ACC | TTT | CTC | TCC | CCT | 716 |
| Tyr | Phe | Ser | Ile | Cys | Pro | Pro | Thr | Glu | Phe | Thr | Thr | Phe | Leu | Ser | Pro | |
| 65 | | | | | 70 | | | | | 75 | | | | | 80 | |
| GAT | GCT | GAG | AAT | CCC | GCG | TAC | CGT | CTG | CCT | AGC | CCC | AAT | GGG | GCA | GAC | 764 |
| Asp | Ala | Glu | Asn | Pro | Ala | Tyr | Arg | Leu | Pro | Ser | Pro | Asn | Gly | Ala | Asp | |
| | | | | 85 | | | | | 90 | | | | | 95 | | |
| GAT | GCC | CGC | CAA | GCA | GTC | GCT | GGA | GCT | GCT | CTC | AAG | ATG | CTG | TCT | TCG | 812 |
| Asp | Ala | Arg | Gln | Ala | Val | Ala | Gly | Ala | Ala | Leu | Lys | Met | Leu | Ser | Ser | |
| | | | 100 | | | | | 105 | | | | | 110 | | | |
| CTA | TAC | ATG | AAG | CCT | GCC | GAC | CCC | AAT | ACC | GGC | ACC | AAC | ATC | TCC | GAC | 860 |
| Leu | Tyr | Met | Lys | Pro | Ala | Asp | Pro | Asn | Thr | Gly | Thr | Asn | Ile | Ser | Asp | |
| | | 115 | | | | | 120 | | | | | 125 | | | | |
| AAT | GCC | TAT | GCT | CAG | CTT | GCC | CTG | GTT | CTC | GAA | CGA | GCA | GTC | GTA | AAG | 908 |
| Asn | Ala | Tyr | Ala | Gln | Leu | Ala | Leu | Val | Leu | Glu | Arg | Ala | Val | Val | Lys | |
| | 130 | | | | | 135 | | | | | 140 | | | | | |
| GTA | CCG | GGT | GGT | GTT | GAT | CGA | GAG | TCA | GTC | AGC | TTC | ATG | TTT | GGT | GAG | 956 |
| Val | Pro | Gly | Gly | Val | Asp | Arg | Glu | Ser | Val | Ser | Phe | Met | Phe | Gly | Glu | |
| 145 | | | | | 150 | | | | | 155 | | | | | 160 | |
| GCT | GTC | GCC | GAT | GTC | TTC | TTT | GCA | CTC | CTC | AAC | GAT | CCT | CGA | GGT | GCT | 1004 |
| Ala | Val | Ala | Asp | Val | Phe | Phe | Ala | Leu | Leu | Asn | Asp | Pro | Arg | Gly | Ala | |
| | | | | 165 | | | | | 170 | | | | | 175 | | |
| TCA | CAG | GAG | GGC | TAC | CAG | CCT | ACC | CCC | GGT | CGT | TAT | AAA | TTC | GAC | GAT | 1052 |
| Ser | Gln | Glu | Gly | Tyr | Gln | Pro | Thr | Pro | Gly | Arg | Tyr | Lys | Phe | Asp | Asp | |
| | | | 180 | | | | | 185 | | | | | 190 | | | |
| GAG | CCT | ACT | CAC | CCA | GTC | GTC | CTA | GTC | CCC | GTA | GAC | CCC | AAC | AAC | CCC | 1100 |
| Glu | Pro | Thr | His | Pro | Val | Val | Leu | Val | Pro | Val | Asp | Pro | Asn | Asn | Pro | |
| | | 195 | | | | | 200 | | | | | 205 | | | | |
| AAC | GGC | CCC | AAG | ATG | CCT | TTC | CGC | CAG | TAT | CAT | GCC | CCA | TTC | TAC | GGC | 1148 |
| Asn | Gly | Pro | Lys | Met | Pro | Phe | Arg | Gln | Tyr | His | Ala | Pro | Phe | Tyr | Gly | |
| | 210 | | | | | 215 | | | | | 220 | | | | | |
| ATG | ACA | ACG | AAG | CGT | TTT | GCC | ACG | CAG | TCC | GAG | CAC | ATC | CTT | GCA | GAC | 1196 |
| Met | Thr | Thr | Lys | Arg | Phe | Ala | Thr | Gln | Ser | Glu | His | Ile | Leu | Ala | Asp | |
| 225 | | | | | 230 | | | | | 235 | | | | | 240 | |
| CCA | CCG | GGT | CTC | CGT | TCT | AAT | GCG | GAT | GAG | ACT | GCT | GAG | TAT | GAC | GAC | 1244 |
| Pro | Pro | Gly | Leu | Arg | Ser | Asn | Ala | Asp | Glu | Thr | Ala | Glu | Tyr | Asp | Asp | |
| | | | | 245 | | | | | 250 | | | | | 255 | | |
| TCT | ATC | CGC | GTG | GCC | ATC | GCC | ATG | GGA | GGT | GCC | CAG | GAT | CTC | AAC | TCC | 1292 |
| Ser | Ile | Arg | Val | Ala | Ile | Ala | Met | Gly | Gly | Ala | Gln | Asp | Leu | Asn | Ser | |
| | | | 260 | | | | | 265 | | | | | 270 | | | |
| ACC | AAG | CGT | AGC | CCA | TGG | CAG | ACG | GCA | CAA | GGT | CTG | TAC | TGG | GCC | TAT | 1340 |
| Thr | Lys | Arg | Ser | Pro | Trp | Gln | Thr | Ala | Gln | Gly | Leu | Tyr | Trp | Ala | Tyr | |
| | 275 | | | | | 280 | | | | | 285 | | | | | |

| | | | | | | | | | | | | | | | | |
|---|---|---|---|---|---|---|---|---|---|---|---|---|---|---|---|---|
| GAT | GGG | TCA | AAC | CTT | GTT | GGA | ACC | CCA | CCG | CGA | TTC | TAC | AAT | CAG | ATT | 1388 |
| Asp | Gly | Ser | Asn | Leu | Val | Gly | Thr | Pro | Pro | Arg | Phe | Tyr | Asn | Gln | Ile | |
| | | 290 | | | | 295 | | | | | 300 | | | | | |
| GTG | CGT | CGC | ATC | GCA | GTG | ACT | TAC | AAG | AAG | GAA | GAT | GAC | CTT | GCC | AAC | 1436 |
| Val | Arg | Arg | Ile | Ala | Val | Thr | Tyr | Lys | Lys | Glu | Asp | Asp | Leu | Ala | Asn | |
| 305 | | | | | 310 | | | | | 315 | | | | | 320 | |
| AGC | GAA | GTC | AAC | AAT | GCT | GAT | TTT | GCC | CGC | CTC | TTC | GCC | CTC | GTC | AAC | 1484 |
| Ser | Glu | Val | Asn | Asn | Ala | Asp | Phe | Ala | Arg | Leu | Phe | Ala | Leu | Val | Asn | |
| | | | | 325 | | | | | 330 | | | | | 335 | | |
| GTC | GCC | TGC | ACA | GAC | GCC | GGC | ATC | TTT | TCC | TGG | AAG | GAA | AAA | TGG | GAG | 1532 |
| Val | Ala | Cys | Thr | Asp | Ala | Gly | Ile | Phe | Ser | Trp | Lys | Glu | Lys | Trp | Glu | |
| | | | 340 | | | | | 345 | | | | | 350 | | | |
| TTT | GAA | TTC | TGG | CGC | CCT | TTG | TCT | GGT | GTG | AGA | GAC | GAT | GGC | CGT | CCA | 1580 |
| Phe | Glu | Phe | Trp | Arg | Pro | Leu | Ser | Gly | Val | Arg | Asp | Asp | Gly | Arg | Pro | |
| | | 355 | | | | | 360 | | | | | 365 | | | | |
| GAC | CAC | GGA | GAT | CCT | TTC | TGG | CTT | ACC | CTC | GGT | GCC | CCA | GCT | ACA | AAC | 1628 |
| Asp | His | Gly | Asp | Pro | Phe | Trp | Leu | Thr | Leu | Gly | Ala | Pro | Ala | Thr | Asn | |
| | 370 | | | | | 375 | | | | | 380 | | | | | |
| ACA | AAC | GAC | ATA | CCC | TTC | AAG | CCT | CCT | TTC | CCC | GCC | TAC | CCA | TCT | GGC | 1676 |
| Thr | Asn | Asp | Ile | Pro | Phe | Lys | Pro | Pro | Phe | Pro | Ala | Tyr | Pro | Ser | Gly | |
| 385 | | | | | 390 | | | | | 395 | | | | | 400 | |
| CAC | GCC | ACC | TTT | GGC | GGT | GCT | GTA | TTC | CAG | ATG | GTC | CGC | CGC | TAC | TAC | 1724 |
| His | Ala | Thr | Phe | Gly | Gly | Ala | Val | Phe | Gln | Met | Val | Arg | Arg | Tyr | Tyr | |
| | | | | 405 | | | | | 410 | | | | | 415 | | |
| AAC | GGG | CGC | GTA | GGC | ACC | TGG | AAG | GAC | GAC | GAA | CCA | GAC | AAC | ATT | GCC | 1772 |
| Asn | Gly | Arg | Val | Gly | Thr | Trp | Lys | Asp | Asp | Glu | Pro | Asp | Asn | Ile | Ala | |
| | | | 420 | | | | | 425 | | | | | 430 | | | |
| ATT | GAC | ATG | ATG | ATA | TCC | GAG | GAG | CTC | AAC | GGC | GTG | AAC | CGC | GAC | CTG | 1820 |
| Ile | Asp | Met | Met | Ile | Ser | Glu | Glu | Leu | Asn | Gly | Val | Asn | Arg | Asp | Leu | |
| | | 435 | | | | | 440 | | | | | 445 | | | | |
| CGC | CAG | CCC | TAC | GAC | CCG | ACT | GCC | CCC | ATC | GAA | GAC | CAA | CCA | GGT | ATC | 1868 |
| Arg | Gln | Pro | Tyr | Asp | Pro | Thr | Ala | Pro | Ile | Glu | Asp | Gln | Pro | Gly | Ile | |
| | 450 | | | | | 455 | | | | | 460 | | | | | |
| GTC | CGC | ACC | CGC | ATC | GTG | CGC | CAC | TTT | GAC | TCA | GCC | TGG | GAA | ATG | ATG | 1916 |
| Val | Arg | Thr | Arg | Ile | Val | Arg | His | Phe | Asp | Ser | Ala | Trp | Glu | Met | Met | |
| 465 | | | | | 470 | | | | | 475 | | | | | 480 | |
| TTC | GAA | AAC | GCC | ATT | TCT | CGC | ATC | TTC | CTC | GGC | GTC | CAC | TGG | CGC | TTC | 1964 |
| Phe | Glu | Asn | Ala | Ile | Ser | Arg | Ile | Phe | Leu | Gly | Val | His | Trp | Arg | Phe | |
| | | | | 485 | | | | | 490 | | | | | 495 | | |
| GAT | GCC | GCC | GCC | GCT | CGC | GAC | ATT | CTG | ATC | CCC | ACC | AAC | ACA | AAG | GAT | 2012 |
| Asp | Ala | Ala | Ala | Ala | Arg | Asp | Ile | Leu | Ile | Pro | Thr | Asn | Thr | Lys | Asp | |
| | | | 500 | | | | | 505 | | | | | 510 | | | |
| GTG | TAT | GCC | GTC | GAC | AGC | AAC | GGC | GCG | ACA | GTG | TTC | CAG | AAT | GTA | GAG | 2060 |
| Val | Tyr | Ala | Val | Asp | Ser | Asn | Gly | Ala | Thr | Val | Phe | Gln | Asn | Val | Glu | |
| | | 515 | | | | | 520 | | | | | 525 | | | | |
| GAT | GTC | AGG | TAC | TCG | ACC | AAG | GGC | ACG | CGT | GAG | GGC | CGC | GAG | GGC | CTC | 2108 |
| Asp | Val | Arg | Tyr | Ser | Thr | Lys | Gly | Thr | Arg | Glu | Gly | Arg | Glu | Gly | Leu | |
| | 530 | | | | | 535 | | | | | 540 | | | | | |
| TTC | CCT | ATC | GGT | GGT | GTG | CCG | CTG | GGT | ATC | GAG | ATT | GCC | GAT | GAG | ATT | 2156 |
| Phe | Pro | Ile | Gly | Gly | Val | Pro | Leu | Gly | Ile | Glu | Ile | Ala | Asp | Glu | Ile | |
| 545 | | | | | 550 | | | | | 555 | | | | | 560 | |
| TTT | AAT | AAT | GGA | CTT | AGG | CCC | ACG | CCG | GAG | CTT | CAG | CCT | ATG | CCG | | 2204 |
| Phe | Asn | Asn | Gly | Leu | Arg | Pro | Thr | Pro | Glu | Leu | Gln | Pro | Met | Pro | | |
| | | | | 565 | | | | | 570 | | | | | 575 | | |
| CAG | GAT | ACC | CCG | GTG | CAG | AAG | CCG | GTT | CAG | GGC | ATG | TGG | GAC | GAG | CAG | 2252 |
| Gln | Asp | Thr | Pro | Val | Gln | Lys | Pro | Val | Gln | Gly | Met | Trp | Asp | Glu | Gln | |
| | | | 580 | | | | | 585 | | | | | 590 | | | |
| GTG | CCG | TTG | GTT | AAG | GAG | GCG | CCG | TAGATGGAGA | GGTTTTCGGC | AGAGTTTACC | | | | | | 2306 |
| Val | Pro | Leu | Val | Lys | Glu | Ala | Pro | | | | | | | | | |
| | | 595 | | | | | 600 | | | | | | | | | |

```
AGTGACGCTG ATGGGCGGTG GAAGGATGTC TGATTTGGCT GAATGTCTTA ATTTGTCAAA      2366

ATTTGGGGTT TGGTTTAGGA TGCTTGCTTG ATACTCTGCG ATTAATACTC CTATTTTGAT      2426

ATTACATAAA TAGAATGCTT TCGGTAGCTG GAATCTGCTG GTTCACTTAT CTTTGTGTCC      2486

GCGTTTGCAT GCTATGAGTG GTTTGCATGT GAGGCTCGAA TTGATATCTG ACCAATTATT      2546

GTTCAGTAAG GCTTGCTTAA ACCTTTTGG TTTCGCAGGA GGGATGGAAA CTGATATATT       2606

TGACTCAGTA GCTAGACACA TAGCAAATGA AATTAAAAAA AAAAAAACTC TATCCTTAAA      2666

GAAAATTAA ACAAACAAAA ATCAGGACAT ATACCATGCG TCTTTCCAGC TCCAAACAC        2726

CTACCACGTT TTATCTTCTG AAACTTTCAC AATGACAGCA CCCACACCCG GCCCCTTCGC      2786

CCACATGCAA GCGCCTCCGG GACCTCCTCA AGCGTC                                2822
```

( 2 ) INFORMATION FOR SEQ ID NO:2:

( i ) SEQUENCE CHARACTERISTICS:
        ( A ) LENGTH: 600 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Ser Val Thr Pro Ile Pro Leu Pro Thr Ile Asp Glu Pro Glu
 1               5                  10                  15

Glu Tyr Asn Asn Asn Tyr Ile Leu Phe Trp Asn Asn Val Gly Leu Glu
                20                  25                  30

Leu Asn Arg Leu Thr His Thr Val Gly Gly Pro Leu Thr Gly Pro Pro
            35                  40                  45

Leu Ser Ala Arg Ala Leu Gly Met Leu His Leu Ala Ile His Asp Ala
        50                  55                  60

Tyr Phe Ser Ile Cys Pro Pro Thr Glu Phe Thr Thr Phe Leu Ser Pro
 65                 70                  75                  80

Asp Ala Glu Asn Pro Ala Tyr Arg Leu Pro Ser Pro Asn Gly Ala Asp
                85                  90                  95

Asp Ala Arg Gln Ala Val Ala Gly Ala Ala Leu Lys Met Leu Ser Ser
               100                 105                 110

Leu Tyr Met Lys Pro Ala Asp Pro Asn Thr Gly Thr Asn Ile Ser Asp
           115                 120                 125

Asn Ala Tyr Ala Gln Leu Ala Leu Val Leu Glu Arg Ala Val Val Lys
       130                 135                 140

Val Pro Gly Gly Val Asp Arg Glu Ser Val Ser Phe Met Phe Gly Glu
145                 150                 155                 160

Ala Val Ala Asp Val Phe Phe Ala Leu Leu Asn Asp Pro Arg Gly Ala
               165                 170                 175

Ser Gln Glu Gly Tyr Gln Pro Thr Pro Gly Arg Tyr Lys Phe Asp Asp
           180                 185                 190

Glu Pro Thr His Pro Val Val Leu Val Pro Val Asp Pro Asn Asn Pro
       195                 200                 205

Asn Gly Pro Lys Met Pro Phe Arg Gln Tyr His Ala Pro Phe Tyr Gly
   210                 215                 220

Met Thr Thr Lys Arg Phe Ala Thr Gln Ser Glu His Ile Leu Ala Asp
225                 230                 235                 240

Pro Pro Gly Leu Arg Ser Asn Ala Asp Glu Thr Ala Glu Tyr Asp Asp
               245                 250                 255

Ser Ile Arg Val Ala Ile Ala Met Gly Gly Ala Gln Asp Leu Asn Ser
```

|     |     |     |     |     | 260 |     |     |     |     | 265 |     |     |     |     | 270 |
|---|---|---|---|---|---|---|---|---|---|---|---|---|---|---|---|

Thr Lys Arg Ser Pro Trp Gln Thr Ala Gln Gly Leu Tyr Trp Ala Tyr
        275                 280                 285

Asp Gly Ser Asn Leu Val Gly Thr Pro Pro Arg Phe Tyr Asn Gln Ile
    290                 295                 300

Val Arg Arg Ile Ala Val Thr Tyr Lys Lys Glu Asp Asp Leu Ala Asn
305                 310                 315                 320

Ser Glu Val Asn Asn Ala Asp Phe Ala Arg Leu Phe Ala Leu Val Asn
                325                 330                 335

Val Ala Cys Thr Asp Ala Gly Ile Phe Ser Trp Lys Glu Lys Trp Glu
            340                 345                 350

Phe Glu Phe Trp Arg Pro Leu Ser Gly Val Arg Asp Asp Gly Arg Pro
        355                 360                 365

Asp His Gly Asp Pro Phe Trp Leu Thr Leu Gly Ala Pro Ala Thr Asn
    370                 375                 380

Thr Asn Asp Ile Pro Phe Lys Pro Pro Phe Pro Ala Tyr Pro Ser Gly
385                 390                 395                 400

His Ala Thr Phe Gly Gly Ala Val Phe Gln Met Val Arg Arg Tyr Tyr
                405                 410                 415

Asn Gly Arg Val Gly Thr Trp Lys Asp Asp Glu Pro Asp Asn Ile Ala
            420                 425                 430

Ile Asp Met Met Ile Ser Glu Glu Leu Asn Gly Val Asn Arg Asp Leu
        435                 440                 445

Arg Gln Pro Tyr Asp Pro Thr Ala Pro Ile Glu Asp Gln Pro Gly Ile
    450                 455                 460

Val Arg Thr Arg Ile Val Arg His Phe Asp Ser Ala Trp Glu Met Met
465                 470                 475                 480

Phe Glu Asn Ala Ile Ser Arg Ile Phe Leu Gly Val His Trp Arg Phe
                485                 490                 495

Asp Ala Ala Ala Ala Arg Asp Ile Leu Ile Pro Thr Asn Thr Lys Asp
            500                 505                 510

Val Tyr Ala Val Asp Ser Asn Gly Ala Thr Val Phe Gln Asn Val Glu
        515                 520                 525

Asp Val Arg Tyr Ser Thr Lys Gly Thr Arg Glu Gly Arg Glu Gly Leu
    530                 535                 540

Phe Pro Ile Gly Gly Val Pro Leu Gly Ile Glu Ile Ala Asp Glu Ile
545                 550                 555                 560

Phe Asn Asn Gly Leu Arg Pro Thr Pro Glu Leu Gln Pro Met Pro
                565                 570                 575

Gln Asp Thr Pro Val Gln Lys Pro Val Gln Gly Met Trp Asp Glu Gln
        580                 585                 590

Val Pro Leu Val Lys Glu Ala Pro
    595                 600

( 2 ) INFORMATION FOR SEQ ID NO:3:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

Xaa Phe Ala Thr Gln Ser Glu His Ile Leu Ala Asp Pro Pro Gly Leu
1               5                   10                  15

Arg Ser Asn Ala Asp Glu Thr Ala Glu Tyr Asp Asp Ser Ile Arg Val
            20                  25                  30

Ala Ile Ala Met Gly Gly Ala Gln Asp Leu Asn
            35                  40

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

Phe Arg Gln Tyr His Ala Pro Phe Tyr Gly Met Thr Thr Lys
1                   5                   10

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

Asp Val Tyr Ala Val Asp Ser Asn Gly Ala Thr Val Phe Gln Asn Val
1                   5                   10                  15

Glu Asp Val Arg Tyr Ser Thr Lys
            20

( 2 ) INFORMATION FOR SEQ ID NO:6:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

Arg Ser Pro Trp Gln Thr Ala Gln Gly Leu Tyr Trp Ala Tyr Asp Gly
1                   5                   10                  15

Ser Asn Leu Val Gly Thr Pro Pro Arg Phe Tyr Asn Gln Ile Val Arg
            20                  25                  30

Arg Ile Ala Val Thr Tyr Lys Lys
            35                  40

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

Phe Asp Asp Glu Pro Thr His Pro Val Val Leu Val Pro Val Asp Pro
1                   5                   10                  15

```
         Asn  Asn  Asn  Asn  Gly  Gly  Lys
                        20
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
   Pro  Ala  Asp  Pro  Asn  Thr  Gly  Thr  Asn  Ile  Ser  Asp  Asn  Ala  Tyr  Ala
   1                   5                        10                       15
   Gln  Leu  Ala  Leu  Val  Leu  Glu  Arg  Ala  Val  Val  Lys
                  20                       25
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
   Met  Leu  Ser  Ser  Leu  Tyr  Met  Lys
   1                   5
```

( 2 ) INFORMATION FOR SEQ ID NO:10:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
   Met  Pro  Phe  Arg  Gln  Tyr  His  Ala  Pro  Phe  Tyr  Gly  Met  Thr  Thr  Lys
   1                   5                        10                       15
```

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
CATGTGGGAC  GAGCAGGTGC  CGTTG                                                   25
```

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GATAGAAAAG TAGGCATCGT GGATA  25

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CAGAGCTCTG GCAGAGAGAG GCGGTCC  27

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CATTGGGGCT AGGCAGACGG TACGC  25

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAAGACAGCA TCTTGAGAGC AGCTC  25

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CAAGCGTAAG CAGCCAAACT GATCT  25

( 2 ) INFORMATION FOR SEQ ID NO:17:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GAGATGTACA TACGTCAGAC CTGGC  25

-continued (2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

GCATATTTAA ATGATGGGGT CCGTTACACC AAT      33

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ATATTAATTA ATCACTGGTA AACTCTGCCG      30

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GAAGAGTACA ACACCAACTA CATA      24

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CCCATCGTAG GCCCAGTATA GGCCCTG      27

HALOPEROXIDASES FROM *CURVULARIA VERRUCULOSA* AND NUCLEIC ACIDS ENCODING SAME

CROSS-REFERENCE TO RELATED APPLICATIONS

This application is a continuation-in-part of U.S. Ser. No. 08/603,534 filed Jul. 11, 1996 now abandoned, which claims the benefit of U.S. Ser. No. 60/001,194 filed Jul. 14, 1995 now abandoned.

BACKGROUND OF THE INVENTION

1. Field of the Invention

The present invention relates to *Curvularia verruculosa* haloperoxidases and isolated nucleic acid fragments comprising nucleic acid sequences encoding the haloperoxidases. The invention also relates to nucleic acid constructs, vectors, and host cells comprising the nucleic acid sequences as well as methods for producing the haloperoxidases. The invention further relates to methods of use of the haloperoxidases.

2. Description of the Related Art

Haloperoxidases catalyze the oxidation of a halide ion ($X=Cl^-$, $Br^-$, or $I^-$) in the presence of hydrogen peroxide ($H_2O_2$) to the corresponding hypohalous acid (HOX):

$$H_2O_2 + X^- + H^+ \rightarrow H_2O + HOX$$

If an appropriate nucleophilic acceptor compound is present, the hypohalous acid will react with the compound to form a halogenated compound. Haloperoxidases can also catalyze peroxidase reactions on certain substrates in the absence of halide ions, but the substrate spectrum is broadened in the presence of halide ions due to unspecific reactions of the substrate and the hypohalide ion.

Haloperoxidases are widespread in nature being produced by mammals, plants, algae, lichen, bacteria, and fungi. Haloperoxidases are probably the enzymes responsible for the formation of naturally occurring halogenated compounds. There are three types of haloperoxidases, classified according to their specificity for halide ions: Chloroperoxidases (E.C. 1.11.1.10) which catalyze the chlorination, bromination and iodination of compounds; bromoperoxidases which show specificity for bromide and iodide ions; and iodoperoxidases (E.C. 1.11.1.8) which solely catalyze the oxidation of iodide ions.

The first discovered haloperoxidases were determined to contain heme as a prosthetic group or co-factor. However, more recently, it has become apparent that there are numerous non-heme haloperoxidases as well. Bacterial haloperoxidases have been found with no prosthetic group. In addition, a number of other non-heme haloperoxidases have been shown to possess a vanadium prosthetic group. Haloperoxidases containing a vanadium prosthetic group are known to include seaweed bromoperoxidases, and at least one type of fungal chloroperoxidase from *Curvularia inaequalis* (van Schijndel et al., 1993, *Biochimica Biophysica Acta* 1161:249–256; Simons et al., 1995, *European Journal of Biochemistry* 229: 566–574; WO 95/27046).

Haloperoxidases, like other oxidoreductases, are of current interest because of their broad range of potential industrial uses. For example, haloperoxidases have been proposed for use as an anti-microbial agent.

It is an object of the present invention to provide new haloperoxidases which can be produced in commercially useful quantities.

SUMMARY OF THE INVENTION

The present invention relates to isolated haloperoxidases obtained from *Curvularia verruculosa* and to isolated nucleic acid fragments comprising a nucleic acid sequence which encodes a *Curvularia verruculosa* haloperoxidase. The present invention further provides nucleic acid constructs, vectors, and recombinant host cells comprising a nucleic acid fragment of the present invention. Furthermore, the present invention provides methods for producing a haloperoxidase of the present invention, compositions, and methods for killing microbial cells or inhibiting growth of microbial cells.

BRIEF DESCRIPTION OF THE FIGURES

FIG. 10 shows the DNA sequence encoding and the deduced amino acid sequence of the *Curvularia verruculosa* haloperoxidase.

FIG. 11 illustrates an alignment of the *Curvularia verruculosa* and the *Curvularia inaequalis* haloperoxidase amino acid sequences.

DETAILED DESCRIPTION OF THE INVENTION

Figure 1:
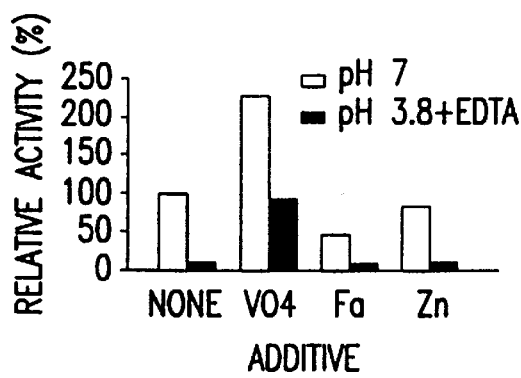
FIG. 1 illustrates the effect of zinc, vanadium, and iron on the activity of the *Curvularia verruculosa* CBS 147.63 haloperoxidase.

The present invention, as mentioned above, relates to haloperoxidases obtained from a *Curvularia verruculosa* strain. In a preferred embodiment, the present invention relates to haloperoxidases obtained from *Curvularia verruculosa* CBS 147.63 or a mutant strain thereof, e.g., the haloperoxidase having the amino acid sequence set forth in SEQ ID NO:2. In another preferred embodiment, the present invention relates to haloperoxidases obtained from *Curvularia verruculosa* CBS 444.70 or a mutant strain thereof.

The physical-chemical properties of the haloperoxidases of the present invention may be determined using various techniques well known in the art. In a preferred embodiment, the haloperoxidases of the present invention contain a vanadium prosthetic group (see FIG. 1). In another preferred embodiment, the haloperoxidases have a mass in the range between about 62 kDa to about 66 kDa as determined by mass spectrometry. In another preferred embodiment, the haloperoxidases of the present invention prefer bromide ion over chloride ion as a substrate. In another preferred embodiment, the haloperoxidases of the present invention have activity over a pH range between about 4 to about 11, preferably between about 5 to about 8. In another preferred embodiment, the haloperoxidases of the present invention have a pH optimum in the range of about 5.25 to about 6.25, preferably about 5.75 (see FIG. 2). In another preferred embodiment, the haloperoxidases of the present invention have a temperature optimum in the range of 50°–70° C., more preferably in the range of 55°–65° C., most preferably about 60° C. (see FIG. 3).

In another preferred embodiment, the haloperoxidases of the present invention retain at least 50% activity, preferably at least 80% activity, after incubation for one hour at pH 7 and 60° C. (see FIG. 4). In another preferred embodiment, the haloperoxidases of the present invention retain at least 50% activity, preferably at least 80% activity, after incubation for one hour at any pH in the range of about 4 to about 11 at 30° C. (see FIG. 5). In another preferred embodiment, the haloperoxidases of the present invention retain at least 50% activity, preferably at least 75% activity, after incubation in the presence of 0.1% $H_2O_2$ for one hour at pH 7 and 60° C. (see FIG. 6).

The present invention also relates to haloperoxidases obtained from fungi which are synonyms of *Curvularia verruculosa* as defined by M. B. Ellis in *Dematiaceous Hyphomycetes,* Commonwealth Mycological Institute, Surrey, England, 1971. The genus Curvularia is a terrestrial member of the group of dematiaceous hyphomycete fungi. *Curvularia verruculosa* spores are usually curved, become rough walled, and usually have only three septa. Strains of *Curvularia verruculosa* are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL), e.g., ATCC 60943–60948, DSM 1157, CBS 147.63, and CBS 444.70.

The present invention also relates to haloperoxidases which are encoded by nucleic acid sequences which are capable of hybridizing under high stringency conditions (for example, prehybridization and hybridization at 45° C. in 5 X SSPE, 0.3% SDS, 200 µg/ml sheared and denatured salmon sperm DNA, and 50% formamide) with a probe which hybridizes with the nucleic acid sequence set forth in SEQ ID NO:1 under the same conditions. The gene, or an oligonucleotide based thereon, can be used as a probe in Southern hybridization to isolate homologous genes of any *Curvularia verruculosa* species. In particular, such probes can be used for hybridization with the genomic or cDNA of the species of interest, following standard Southern blotting procedures, in order to identify and isolate the corresponding haloperoxidase gene thezein. A PCR reaction using the degenerate probes mentioned herein and genomic DNA or first-strand cDNA from a *Curvularia verruculosa* species can also yield a *Curvularia verruculosa* haloperoxidase-specific product which can then be used as a probe to clone the corresponding genomic or cDNA.

Identification and isolation of haloperoxidase genes from a source other than those specifically exemplified herein can be achieved by utilization of the methodology described in the present examples, from publicly available *Curvularia verruculosa* strains.

For purposes of the present invention, the term "obtained from" means that the haloperoxidase is produced by a specific source, e.g., a *Curvularia verruculosa* strain, or by a cell in which a gene from the source encoding the haloperoxidase has been inserted.

The invention also encompasses haloperoxidase variants which have at least about 93%, preferably about 95%, more preferably about 97%, and even more preferably 99% homology with the amino acid sequence depicted in FIG. 10 (SEQ ID NO:2), and which qualitatively retains the activity of the proteins described herein. The invention is also directed to haloperoxidase variants which have an amino acid sequence which differs by no more than three amino acids, more preferably by no more than two amino acids, and most preferably by one amino acid from the amino acid sequence set forth in SEQ ID NO:2. Each difference may be an insertion or deletion of an amino acid or the substitution of an amino acid residue by a different amino acid. Useful substitutions include ones in which conservative amino acid substitutions have been made, which substitutions do not significantly affect the activity of the protein. By conservative substitution is meant that amino acids of the same class may be substituted by any other amino acid of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

The haloperoxidase of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF)), differential solubility (e.g., ammonium sulfate precipitation), or extraction (see, for example, *Protein Purification,* eds. J.-C. Janson and Lars Ryden, VCH Publishers, New York, 1989). As defined herein, an "isolated" haloperoxidase is a haloperoxidase which is essentially free of other non-haloperoxidase proteins, for example, at least about 20% pure, preferably at least about 40% pure, more preferably about 60% pure, even more preferably about 80% pure, most preferably about 90% pure, and even most preferably about 95% pure, as determined by SDS-PAGE.

Nucleic Acid Fragments and Constructs

The present invention also relates to nucleic acid fragments comprising a nucleic acid sequence which encodes a haloperoxidase of the present invention and to nucleic acid constructs comprising a nucleic acid fragment of the present invention.

In a preferred embodiment, the nucleic acid sequence encodes a haloperoxidase obtained from *Curvularia verruculosa* CBS 147.63, e.g., the nucleic acid sequence set forth in SEQ ID NO:1, or CBS 444.70. The present invention also encompasses nucleic acid sequences which encode a haloperoxidase having the amino acid sequence set forth in SEQ ID NO:2, which differ from SEQ ID NO:1 by virtue of the degeneracy of the genetic code. The nucleic acid sequences of the present invention further encompass both the genomic sequence depicted therein as well as the corresponding cDNA and RNA sequences, and the phrase "nucleic acid sequences" as used herein will be understood to encompass all such variations including synthetic DNA.

The present invention also relates to nucleic acid constructs comprising a nucleic acid fragment of the invention. "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a preferred embodiment, the nucleic acid constructs are operably linked to regulatory regions capable of directing the expression of the haloperoxidase in a suitable expression host.

The present invention also provides recombinant vectors comprising a nucleic acid construct of the present invention. In a preferred embodiment, the nucleic acid sequence is operably linked to a promoter sequence. In another preferred embodiment, the vectors of the present invention further comprise a transcription termination signal and/or a selectable marker.

The recombinant vectors of the invention are useful for the expression of the *Curvularia verruculosa* haloperoxidase gene in active form. A useful expression vector contains an element that permits stable integration of the vector into the host cell genome or autonomous replication of the vector in a host cell independent of the genome of the host cell, and preferably one or more phenotypic markers which permit easy selection of transformed host cells. The vector may also include control sequences such as a promoter, ribosome binding site, translation initiation signal, and, optionally, a repressor gene, a selectable marker or various activator genes. To permit the secretion of the expressed protein, nucleic acids encoding a signal sequence may be inserted prior to the coding sequence of the gene. For expression under the direction of control sequences, a haloperoxidase gene to be used according to the present invention is operably linked to the control sequences in the proper reading frame.

The vector carrying the nucleic acid construct of the present invention may be any vector which can conveniently be subjected to recombinant DNA procedures. The choice of a vector will typically depend on the host cell into which the vector is to be introduced. The vector may be an autonomously replicating vector, i.e., a vector which exists as an extrachromosomal entity, the replication of which is independent of chromosomal replication, e.g. a plasmid, an extrachromosomal element, a minichromosome, or an artificial chromosome. Alternatively, the vector may be one which, when introduced into a host cell, is integrated into the host cell genome and replicated together with the chromosome(s) into which it has been integrated. The vector system may be (a single vector or plasmid or two or more vectors or plasmids which together contain the total DNA to be integrated into the genome.

In the vector, the DNA sequence should be operably linked to a suitable promoter sequence. The promoter may be any DNA sequence which shows transcriptional activity in the host cell of choice and may be obtained from genes encoding proteins either homologous or heterologous to the host cell. Examples of suitable promoters for directing the transcription of the nucleic acid constructs of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyQ), the promoters of the *Bacillus amyloliquefaciens* α-amylase (amyQ), the promoters of the *Bacillus subtilis* xylA and xylB genes, the prokaryotic β-lactamase promoter (Villa-Kamaroff et al., 1978, *Proceedings of the National Academy of Sciences USA* 75:3727–3731), or the tac promoter (DeBoer et al., 1983, *Proceedings of the National Academy of Sciences USA* 80:21–25). Further promoters are described in "Useful proteins from recombinant bacteria" in *Scientific American,* 1980, 242:74–94; and in Sambrook et al., *Molecular Cloning, A Laboratory Manual,* 2d ed., Cold Spring Harbor, N.Y., 1989. In a yeast host, a useful promoter is the eno-1 promoter. For transcription in a fungal host, examples of useful promoters are those obtained from the gene encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Preferred promoters are the TAKA-amylase and glaA promoters.

The vector of the invention may also comprise a suitable transcription terminator and, in eukaryotes, polyadenylation sequences operably connected to the DNA sequence encoding a haloperoxidase of the present invention. Termination and polyadenylation sequences may be obtained from the same sources as the promoter. The vector may further comprise a DNA sequence enabling the vector to replicate in the host cell in question. Examples of such sequences are the origins of replication of plasmids pUC19, pACYC177, pUB110, pE194, pAMB1, and pIJ702.

The vector may also comprise a selectable marker, e.g., a gene the product of which complements a defect in the host cell, such as the dal genes from *Bacillus subtilis* or *Bacillus licheniformis,* or one which confers antibiotic resistance such as ampicillin, kanamycin, chloramphenicol or tetracycline resistance. Examples of Aspergillus selection markers include amdS, pyrG, argB, niaD, sC, trpC, and hygB, a marker giving rise to hygromycin resistance. Preferred for use in an Aspergillus host cell are the amdS and pyrG markers of *Aspergillus nidulans* or *Aspergillus oryzae*. A frequently used mammalian marker is the dihydrofolate reductase (DHFR) gene. Furthermore, selection may be accomplished by co-transformation, e.g., as described in WO 91/17243.

To avoid the necessity of disrupting the cell to obtain the expressed haloperoxidase, and to minimize the amount of possible degradation of the expressed haloperoxidase within the cell, it is preferred that expression of the haloperoxidase gene gives rise to a product secreted outside the cell. To this end, the haloperoxidases of the present invention may thus comprise a preregion permitting secretion of the expressed protein into the fermentation medium. If desirable, this preregion may be native to a haloperoxidase of the invention or substituted with a different preregion or signal sequence, conveniently accomplished by substitution of the DNA sequences encoding the respective preregions. For example, the preregion may be obtained from a glucoamylase or an amylase gene from an Aspergillus species, an amylase gene from a Bacillus species, a lipase or proteinase gene from *Rhizomucor miehei,* the gene for the α-factor from *Saccharomyces cerevisiae* or the calf preprochymosin gene. Particularly preferred is the preregion for *Aspergillus oryzae* TAKA amylase, *Aspergillus niger* neutral amylase, the maltogenic amylase from Bacillus NCIB 11837, *Bacillus stearothennophilus* α-amylase, or *Bacillus licheniformis* subtilisin. An effective signal sequence for fungal hosts is the *Aspergillus oryzae* TAKA amylase signal, the *Rhizomucor miehei* aspartic proteinase signal, or the *Rhizomucor miehei* lipase signal.

The procedures used to ligate the nucleic acid construct of the invention, the promoter, terminator and other elements, respectively, and to insert them into suitable vectors containing the information necessary for replication, are well known to one skilled in the art (cf., for instance, Sambrook et al., supra).

The present invention also relates to host cells comprising a nucleic acid construct or an expression vector of the invention which are advantageously used in the recombinant production of the haloperoxidases of the invention. The cell may be transformed with the nucleic acid construct of the invention, conveniently by integrating the construct into the host chromosome. This integration is generally considered to be an advantage as the sequence is more likely to be stably maintained in the cell. Integration of the construct into the host chromosome may be performed according to conventional methods, e.g., by homologous or heterologous recombination. Alternatively, the cell may be transformed with an expression vector as described below in connection with the different types of host cells.

The choice of host cells and vectors will to a large extent depend upon the haloperoxidase and its source. The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram negative bacteria such as *E. coli.* The transformation of the bacteria may, for instance, be effected by protoplast transformation or by using competent cells in a manner known per se.

The host cell is preferably a eukaryote, such as a mammalian cell, an insect cell, a plant cell or preferably a fungal cell, including yeast and filamentous fungi. For example, useful mammalian cells include CHO or COS cells. A yeast host cell may be selected from a species of Saccharomyces or Schizosaccharomyces, e.g., *Saccharomyces cerevisiae.* Useful filamentous fungi may be selected from a species of Aspergillus, e.g., *Aspergillus oryzae* or *Aspergillus niger.* Alternatively, a strain of a Fusarium species, e.g., *Fusarium oxysporum* or *Fusarium graminearum,* can be used as a host cell. Fungal cells may be transformed by a process involving protoplast formation, transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989, *Gene* 78:147–156 or in copending U.S. Ser. No. 08/269,449.

In a particularly preferred embodiment, the expression of the haloperoxidase gene is achieved in a fungal host cell, such as Aspergillus. The haloperoxidase gene is ligated into a plasmid preferably containing the *Aspergillus oryzae* TAKA amylase promoter or the *Aspergillus niger* neutral amylase NA2 promoter and amdS or pyrG as the selectable marker. Alternatively, the selectable marker may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, Proceedings of the National Academy of Sciences USA 81:1470–1474.

Methods for Producing the Haloperoxidases of the Present Invention

The present invention also relates to methods for producing a haloperoxidase of the present invention comprising (a) fermenting a *Curvularia verruculosa* strain to produce a supernatant comprising the haloperoxidase; and (b) recovering the haloperoxidase.

The present invention also relates to methods for recombinantly producing a haloperoxidase of the present invention comprising (a) fermenting a host cell comprising a nucleic acid construct comprising a nucleic acid sequence encoding the haloperoxidase under conditions conducive to the production of the enzyme and (b) recovering the haloperoxidase. If the expression system secretes the haloperoxidase into the fermentation medium, the enzyme can be recovered directly from the medium. If the recombinant haloperoxidase is not secreted, it is recovered from cell lysates.

As defined herein, the term "fermentation" is any method of cultivation of a cell resulting in the expression or isolation of the haloperoxidase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the haloperoxidase to be expressed or isolated.

The fermentation takes place in a suitable nutrient medium comprising carbon and nitrogen sources and inorganic salts, using procedures known in the art (see, e.g., Bennett, J. W. and LaSure, L. (eds.), *More Gene Manipulations in Fungi,* Academic Press, CA, 1991). Suitable media are available from commercial suppliers or may be prepared according to published compositions (e.g., in catalogues of the American Type Culture Collection).

The resulting haloperoxidases produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

Uses

The present invention is further directed to methods of oxidizing a halide ion to the corresponding hypohalous acid, comprising reacting the halide ion and a source of hydrogen peroxide in the presence of a haloperoxidase of the invention. The present invention also relates to methods of halogenating a compound comprising reacting the compound, a halide ion and a source of hydrogen peroxide in the presence of a haloperoxidase of the invention.

The present invention also relates to methods for killing or inhibiting the growth of microbial cells, comprising contacting the cells with a haloperoxidase of the invention, a source of hydrogen peroxide, and a source of thiocyanate in an aqueous solution.

The source of hydrogen peroxide can be hydrogen peroxide itself or a hydrogen peroxide precursor, such as, a percarbonate, perborate, peroxycarboxylic acid or a salt thereof. Furthermore, the source may be a hydrogen peroxide generating enzyme system, such as an oxidase, e.g., a glucose oxidase, glycerol oxidase or amino acid oxidase, and its substrate. The hydrogen peroxide source may be added in a concentration corresponding to a hydrogen peroxide concentration in the range of from about 0.001 to about 10 mM, preferably about 0.01 to about 1 mM.

The thiocyanate source may be thiocyanate itself or a salt thereof, e.g., sodium or potassium. Furthermore, if the reaction occurs orally, thiocyanate is endogenous to the saliva. The thiocyanate source may be added in a concentration corresponding to a thiocyanate concentration in the range of from about 0.001 to about 10 mM, preferably about 0.01 to about 1 mM.

The haloperoxidases may be used as preservation agents and disinfection agents such as in water based paints and personal care products, e.g., toothpaste, mouthwash, skin care creams and lotions, hair care and body care formulations, solutions for cleaning contact lenses and dentures. The haloperoxidases also may be used for cleaning surfaces and cooking utensils in food processing plants and in any area in which food is prepared or served. The haloperoxidases also may be used in enzymatic bleaching applications, e.g., pulp bleaching and stain bleaching (in detergent compositions).

The concentration of the haloperoxidase in the methods of use of the present invention, is preferably in the range of 0.0001 HU/ml–10 HU/ml, more preferably in the range of 0.001–1 HU/ml (as defined below).

The present invention is further illustrated in the following examples which is not in any way intended to limit the scope of the invention as claimed.

EXAMPLES

Example 1

Cultivation of *Curvularia verruculosa* CBS 147.63

*Curvularia verruculosa* CBS 147.63 is grown for 165 hours at 26° C. and 250 rpm in a 2 l fermentor having a fermentation medium comprising the following components:

| | |
|---|---|
| Glucose | 15 g/l |
| Yeast Extract | 4 g/l |
| $K_2HPO_4$ | 1 g/l |
| $MgSO_4 \cdot 7H_2O$ | 0.5 g/l |
| $VOSO_4$ | 167 mg/l |

The medium is adjusted to pH 7.2 before autoclaving. The fermentor is inoculated directly from agar slants suspended with 10 ml of sterilized $H_2O$ containing 0.1% Tween where 2.5 ml of the suspension is used to inoculate each shake flask. The supernatant is recovered by centrifuging the whole broth, and is washed and concentrated 24 fold using a Filtron apparatus with a 10 kDa cutoff membrane.

Example 2

Haloperoxidase Assays

Microtiter assays are performed by mixing 100 µl of haloperoxidase sample (about 0.2 µg/ml) and 100 µl of 0.3M sodium phosphate pH 7 buffer-0.5M potassium bromide-0.08% phenol red, adding the solution to 10 µl of 0.3% $H_2O_2$, and measuring the absorption at 595 nm as a function of time.

Assays using monochlorodimedone (Sigma M4632, $\epsilon=20000 M^{-1} cm^{-1}$ at 290 nm) as a substrate are performed as described below. The decrease in absorption at 290 nm is measured as a function of time. Assays are performed in 0.1M sodium phosphate or 0.1M sodium acetate, 50 µM monochlorodimedone, 10 mM KBr/KCl, and 1 mM $H_2O_2$ using a haloperoxidase concentration of about 1 µg/ml. One HU is defined as 1 micromol of monochlorodimedone chlorinated or brominated per minute at pH 5 and 30° C. Temperature, pH and $H_2O_2$ stability experiments are carried out by preincubating the haloperoxidase under the given conditions and then assaying residual activity in the microtiter assay.

Example 3

Purification of *Curvularia verruculosa* CBS 147.63 haloperoxidase

Thirty ml of concentrated supernatant from the whole broth described in Example 1 are loaded onto a 30 ml Q-Sepharose column (XK 16/60) equilibrated with 10 mM potassium phosphate pH 7.0 buffer and eluted with a 300 ml linear gradient of sodium chloride from 0 to 1M at a flow of 2 ml/minute. Fractions of 3 ml are collected, and fractions containing haloperoxidase activity are pooled, concentrated (Centricon-10, Amicon) and subjected to gel filtration on a HiLoad Superdex 75 (16/60) column (Pharmacia) equilibrated in 50 mM sodium phosphate pH 7.1 buffer and eluted in the same buffer at a flow rate of 1 ml/min. Fractions of 1.5 ml are collected. Haloperoxidase assays are performed as described in Example 2.

Example 4

Characterization of *Curvularia verruculosa* CBS 147.63 haloperoxidase

The haloperoxidase purified as described in Example 3 is pretreated for 45 minutes in 0.3M sodium phosphate pH 7 buffer (control) or in 0.1M sodium citrate-10 mM EDTA pH 3.8. After the pretreatment, the haloperoxidase is treated for 2 hours with 10 mM additive in 0.2M Tris-HCl pH 7.5 where the additive is either $Na_3VO_4$, $FeCl_2$ or $ZnCl_2$.

FIG. 1 shows that the haloperoxidase loses activity when treated with EDTA indicating the presence of a prosthetic group necessary for activity. The addition of zinc or iron had no effect on the activity of the haloperoxidase. However, the addition of vanadate resulted in the haloperoxidase regaining activity, indicating that it contains a vanadium prosthetic group.

Figure 2:
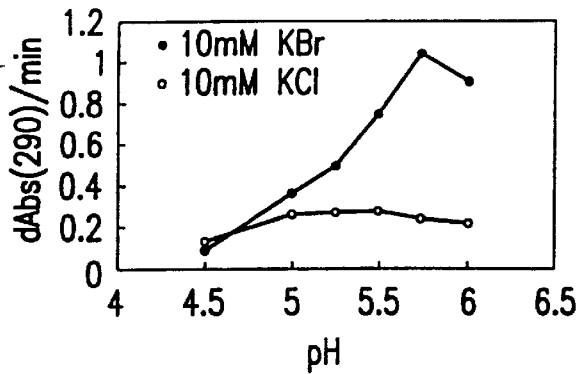
FIG. 2 shows the effect of pH at 30° C. on the activity of the *Curvularia verruculosa* CBS 147.63 haloperoxidase.

The pH optimum and specificity toward $Br^-$ and $Cl^-$ of the haloperoxidase is determined in 0.1M sodium acetate buffer containing 50 mM monochlorodimedone, 1 mM $H_2O_2$, 10 mM KBr or KCl, and 0.4 µg/ml haloperoxidase (extinction coefficient=2.6 l/(g*cm), 30° C. As shown in FIG. 2, the haloperoxidase prefers $Br^-$ to $Cl^-$ as a substrate and has a pH optimum of about 5.75.

Figure 3:
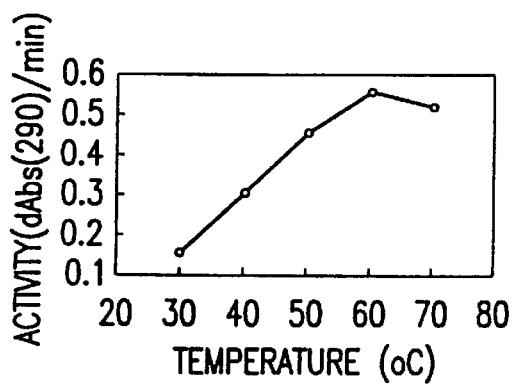
FIG. 3 illustrates the effect of temperature at pH 5.5 on the activity of the *Curvularia verruculosa* CBS 147.63 haloperoxidise.

The temperature optimum of the haloperoxidase in 0.1M sodium acetate pH 5.5 buffer containing 50 mM monochlorodimedone, 10 mM KBr, 1 mM $H_2O_2$, and 0.1 µg/ml enzyme is about 60° C. (FIG. 3).

Figure 4:
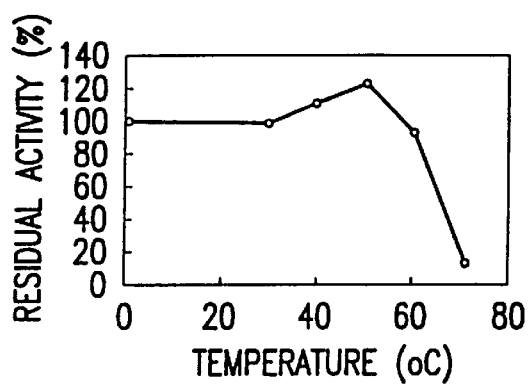
FIG. 4 shows the effect of temperature at pH 7 on the stability of the *Curvularia verruculosa* CBS 147.63 haloperoxidase.

The stability of the haloperoxidase as a function of temperature is determined by preincubating the haloperoxidase for 1 hour at the given temperature in 20 mM sodium phosphate pH 7 buffer. The results show that the haloperoxidase remains stable for at least one hour at temperatures up to 60° C. (FIG. 4).

Figure 5:
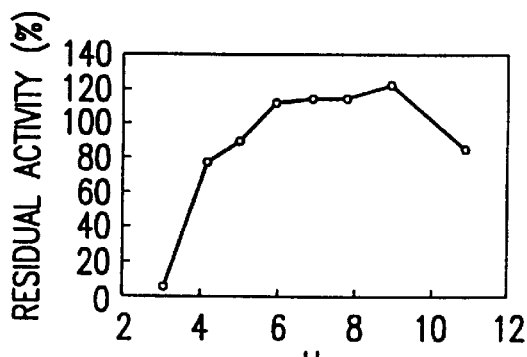
FIG. 5 illustrates the effect of pH at 30° C. on the stability of the *Curvularia verruculosa* CBS 147.63 haloperoxidase.

The haloperoxidase (4 µg/ml) is also stable over a broad range of pH as shown in FIG. 5 retaining more than 80% activity after one hour incubations at 30° C. in 20 mM Britten-Robinson buffer at varying pH from 5 to 11 (control at pH 7, 4° C.).

Figure 6:
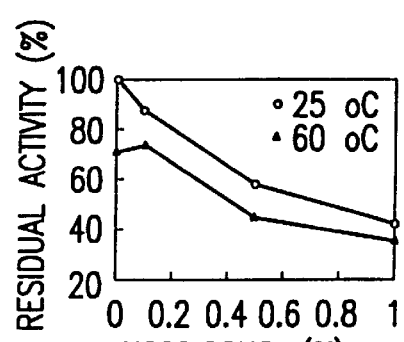
FIG. 6 shows the effect of $H_2O_2$ concentration at pH 7 and 60° C. on the stability of the *Curvularia verruculosa* CBS 147.63 haloperoxidase.

Furthermore, the haloperoxidase (3 µg/ml) is highly stable in the presence of $H_2O_2$, retaining 75% residual activity after one hour incubation at 60° C. in the presence of 0.1% $H_2O_2$ in 50 mM sodium phosphate pH 7 (FIG. 6).

Example 5

Amino acid sequencing *Curvularia verruculosa* CBS 147.63 haloperoxidase

Reduced and S-carboxymethylated *Curvularia verruculosa* CBS 147.63 haloperoxidase (≈1 mg) is digested with 10 µg of the lysyl-specific protease from Achromobacter in 20 mM NH$_4$HCO$_3$ for 16 hours at 37° C. The resulting peptides are separated by reverse phase HPLC using a Vydac C18 column and 0.1% trifluoroacetic acid (TFA) as Solvent A and 80% 2-propanol containing 0.08% TFA as Solvent B. The column is first equilibrated with 5% Solvent B (which equals 95% of Solvent A). The column is then washed with 5% Solvent B for 5 minutes after injection of the peptide mixture. The bound peptides are finally eluted at a flow rate of 150 µl/minute with a linear gradient of Solvent B where the gradient runs over 85 minutes and ends at 90 minutes total time with 90% Solvent B (which equals 10% of Solvent A). The peptides are repurified using a linear gradient involving 0.1% TFA as Solvent A and 80% acetonitrile containing 0.08% TFA as Solvent B at a flow rate of 250 µl/min.

Amino acid sequencing is carried out on an Applied Biosystems 473A Protein Sequencer according to the manufacturer's instructions.

In the process of direct amino acid sequencing, it becomes apparent that the N-terminal of the protein is blocked, and therefore not accessible to be sequenced. However, the sequence of eight internal peptides is determined. The sequences obtained are as follows (SEQ ID NOS:3–10).

Peptide 1:
Xaa-Phe-Ala-Thr-Gln-Ser-Glu-His-Ile-Leu-Ala-Asp-Pro-Pro-Gly-Leu-Arg-Ser-Asn-Ala-Asp-Glu-Thr-Ala-Glu-Tyr-Asp-Asp-Ser-Ile-Arg-Val-Ala-Ile-Ala-Met-Gly-Gly-Ala-Gln-Asp-Leu-Asn (SEQ ID NO:3)

Peptide 2:
Phe-Arg-Gln-Tyr-His-Ala-Pro-Phe-Tyr-Gly-Met-Thr-Thr-Lys (SEQ ID NO:4)

Peptide 3:
Asp-Val-Tyr-Ala-Val-Asp-Ser-Asn-Gly-Ala-Thr-Val-Phe-Gln-Asn-Val-Glu-Asp-Val-Arg-Tyr-Ser-Thr-Lys (SEQ ID NO:5)

Peptide 4:
Arg-Ser-Pro-Trp-Gln-Thr-Ala-Gln-Gly-Leu-Tyr-Trp-Ala-Tyr-Asp-Gly-Ser-Asn-Leu-Val-Gly-Thr-Pro-Pro-Arg-Phe-Tyr-Asn-Gln-Ile-Val-Arg-Arg-Ile-Ala-Val-Thr-Tyr-Lys-Lys (SEQ ID NO:6)

Peptide 5:
Phe-Asp-Asp-Glu-Pro-Thr-His-Pro-Val-Val-Leu-Val-Pro-Val-Asp-Pro-Asn-Asn-Asn-Asn-Gly-Gly-Lys (SEQ ID NO:7)

Peptide 6:
Pro-Ala-Asp-Pro-Asn-Thr-Gly-Thr-Asn-Ile-Ser-Asp-Asn-Ala-Tyr-Ala-Gln-Leu-Ala-Leu-Val-Leu-Glu-Arg-Ala-Val-Val-Lys (SEQ ID NO:8)

Peptide 7:
Met-Leu-Ser-Ser-Leu-Tyr-Met-Lys (SEQ ID NO:9)

Peptide 8:
Met-Pro-Phe-Arg-Gln-Tyr-His-Ala-Pro-Phe-Tyr-Gly-Met-Thr-Thr-Lys (SEQ ID NO:10)

Peptide 8 is identical to Peptide 2, except for two additional amino acid residues at the N-terminus.

Example 6

Amino acid analysis of *Curvularia verruculosa* CBS 147.63 haloperoxidase

Hydrolysis for amino acid analysis is carried out in duplicate. Lyophilized samples are hydrolyzed in evacuated sealed glass vials containing 100 µl 6N HCl, 0.1% phenol for 16 hours at 110° C. Analysis is performed using an Applied Biosystems 420A Amino Acid Analysis System according to the manufacturer's instructions.

The results of the amino acid composition determination are presented in Table 1 (the values are an average of four determinations).

TABLE 1

Amino acid composition of the haloperoxidase from *Curvularia verruculosa*. ND = not determined.

| Amino acid | Composition (mol %) |
|---|---|
| Aspartic acid | 15.1 |
| Glutamic acid | 8.6 |
| Serine | 4.8 |
| Glycine | 8.0 |
| Histidine | 1.8 |
| Arginine | 6.0 |
| Threonine | 6.3 |
| Alanine | 9.5 |
| Proline | 9.6 |
| Tyrosine | 3.7 |
| Valine | 5.8 |
| Methionine | 1.7 |
| Cysteine | ND |
| Isoleucine | 4.3 |
| Leucine | 6.9 |
| Phenylalanine | 5.1 |
| Lysine | 2.7 |
| Tryptophan | ND |

Example 7

SDS-PAGE and IEF of *Curvularia verruculosa* CBS 147.63 haloperoxidase

SDS-PAGE (Novex) and IEF (Pharmacia) are performed according to the manufacturer's instructions. The IEF gel is stained for haloperoxidase activity using phenol red reagent and $H_2O_2$.

SDS-PAGE demonstrates that the haloperoxidase has a molecular weight of about 68 kDa, while IEF indicates the haloperoxidase has an isoelectric point of about 3.8.

Example 8

Carbohydrate analysis of *Curvularia verruculosa* CBS 147.63 haloperoxidase

Hydrolysis of protein-bound carbohydrate for monosaccharide composition analysis is performed in duplicate. Lyophilized samples are hydrolyzed in evacuated sealed glass tubes with 100 µl 2M TFA for 1 hour and 4 hours at 100° C. Monosaccharides are separated by high performance anion exchange chromatography using a Dionex PA1 column eluted with 16 mM NaOH and detected by pulsed amperometric detection.

Monosaccharide composition analysis shows that the haloperoxidase is glycosylated as shown in Table 2 (the values are an average of four determinations). The absence of glucosamine in the analysis suggests that the carbohydrate is likely O-linked. Interestingly, glucose is not usually found in glycoproteins.

TABLE 2

Monosaccharide composition of the haloperoxidase from *Curvularia verruculosa*.

| Monosaccharide | Concentration of Monosaccharide (pmol/pmol haloperoxidase) |
| --- | --- |
| Galactose | 3 |
| Glucose | 16 |
| Mannose | 29 |

Example 9

Mass spectrometry of *Curvularia verruculosa* CBS 147.63 haloperoxidase

Mass spectrometry is performed using matrix assisted laser desorption ionization time-of flight mass spectrometry in a VG Analytical TofSpec. For mass spectrometry, 2 μl of the haloperoxidase are mixed with 2 μl of saturated matrix solution (α-cyano-4-hydroxycinnamic acid in 0.1% TFA:acetonitrile (70:30)) and 2 μl of the mixture spotted onto the target plate. Before introduction into the mass spectrometer, the solvent is removed by evaporation. Samples are desorbed and ionized by 4 ns laser pulses (337 nm) at threshold laser power and accelerated into the field-free flight tube by an accelerating voltage of 25 kV. Ions are detected by a microchannel plate set at 1850 V. Intact haloperoxidase as well as all initial peptide fractions are analyzed by mass spectrometry.

Mass spectrometry clearly shows that the glycosylation of the haloperoxidase is heterogeneous. The average mass of the haloperoxidase is around 64,500 Da, which is in reasonable agreement with the molecular weight of 68 kDa determined by SDS-PAGE. The mass of the haloperoxidase ranges from 62 kDa to 66 kDa.

Example 10

Specific activity determination of *Curvularia verruculosa* CBS 147.63 haloperoxidase Specific activity of the *Curvularia verruculosa* CBS 147.63 haloperoxidase is determined under the following conditions: 0.1M sodium acetate, 50 μM monochlorodimedone, 1 mM $H_2O_2$, and 10 mM KCl at pH 5 and 30° C.

A specific activity of 13 $HU/A_{280}$ is determined, corresponding to a specific activity of 33.8 U/mg haloperoxidase, based on the measured extinction coefficient of 2.6 l/(g*cm). Under similar conditions, the specific activity reported by Simons et al., supra, for the *Curvularia inaequalis* haloperoxidase is 7.5 U/mg. Thus, it appears that the *Curvularia verruculosa* enzyme has about a four-fold higher specific activity than that of *Curvularia inaequalis*.

Example 11

Genomic DNA extraction

*Curvularia verruculosa* CBS 147.63 is grown in 25 ml of 0.5% yeast extract-2% glucose (YEG) medium for 24 hours at 32° C. and 250 rpm. Mycelia are then collected by filtration through Miracloth (Calbiochem, La Jolla, Calif.) and washed once with 25 ml of 10 mM Tris-1 mM EDTA (TE) buffer. Excess buffer is drained from the mycelia preparation which is subsequently frozen in liquid nitrogen. The frozen mycelia preparation is ground to a fine powder in an electric coffee grinder, and the powder is added to a disposable plastic centrifuge tube containing 20 ml of TE buffer and 5 ml of 20% w/v sodium dodecylsulfate (SDS). The mixture is gently inverted several times to ensure mixing, and extracted twice with an equal volume of phenol:chloroform:isoamyl alcohol (25:24:1 v/v/v). Sodium acetate (3M solution) is added to the extracted sample to a final concentration of 0.3M followed by 2.5 volumes of ice cold ethanol to precipitate the DNA. The tube is centrifuged at 15,000×g for 30 minutes to pellet the DNA. The DNA pellet is allowed to air-dry for 30 minutes before resuspension in 0.5 ml of TE buffer. DNase-free ribonuclease A is added to the resuspended DNA pellet to a concentration of 100 μg/ml and the mixture is then incubated at 37° C. for 30 min. Proteinase K (200 μg/ml) is added and the tube is incubated an additional one hour at 37° C. Finally, the sample is extracted twice with phenol:chloroform:isoamyl alcohol and the DNA precipitated with ethanol. The precipitated DNA is washed with 70% ethanol, dried under vacuum, resuspended in TE buffer, and stored at 4° C.

Example 12

PCR amplification of *Curvularia verruculosa* CBS 147.63 haloperoxidase gene segments Based on the amino acid sequences of the *Curvularia verruculosa* CBS 147.63 haloperoxidase described above and of the *Curvularia inaequalis* haloperoxidase disclosed by Simons et al., supra, the oligonucleotide primers shown below are synthesized with an Applied Biosystems Model 394 DNA/RNA Synthesizer, according to the manufacturer's instructions, for use to PCR amplify haloperoxidase gene fragments from *Curvularia verruculosa* CBS 147.63:

Forward primer: dGAAGAGTACAACACCAACTACATA (SEQ ID NO:20)
Reverse primer: dCCCATCGTAGGCCCAGTATAGGC-CCTG (SEQ ID NO:21)

Amplification reactions (100 μl) are prepared using approximately 1 μg of *Curvularia verruculosa* CBS 147.63 genomic DNA as the template. Each reaction contains the following components: 1 μg genomic DNA, 40 pmol forward primer, 40 pmol reverse primer, 200 μM each dNTP, 1×Taq polymerase buffer (Perkin-Elmer Corp., Branchburg, N.J.), and 5 Units of Taq polymerase (Perkin-Elmer Corp., Branchburg, N.J.). Sterile mineral oil (100 μl) is layered on top of each reaction mixture, and the reactions are incubated in a Perkin-Elmer Model 480 Thermal Cycler programmed as follows: Cycle 1-95° C. for 5 minutes, 45° C. for 2 minutes, and 67° C. for 5 minutes; Cycle 2-30°–95° C for 2 minutes; 45° C. for 2 minutes, and 67° C. for 2 minutes; and Soak cycle at 4° C. The reaction products are isolated on a 1% low melting point agarose gel (Sigma Chemical Co., St. Louis, Mo.). The product bands are excised from the gel and purified using β-agarase (New England Biolabs, Beverly, Mass.) according to the manufacturer's instructions. The purified PCR products are subsequently cloned into a pCRII vector (Invitrogen, San Diego, Calif.) and the DNA sequences are determined using lac forward and reverse primers (New England BioLabs, Beverly, Mass.).

Figure 7:
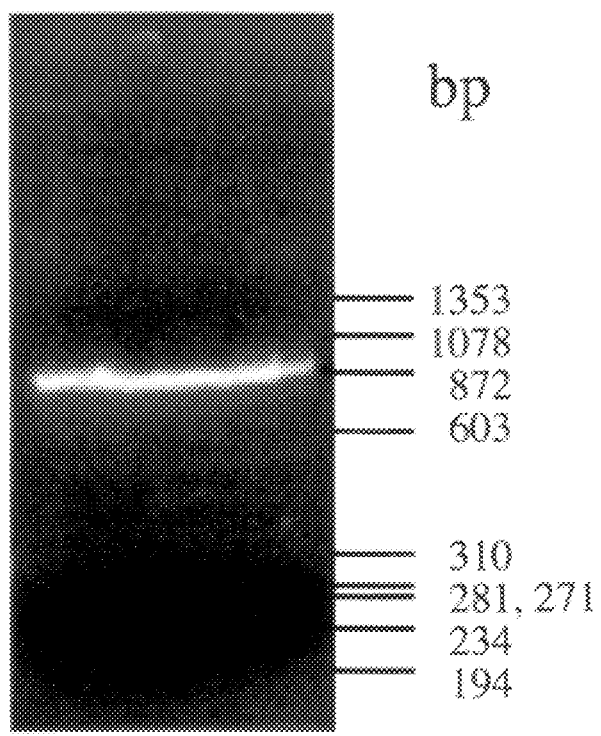
FIG. 7 illustrates an agarose electrophoretic gel of the product from PCR amplification of the haloperoxidase-specific gene sequences using *Curvularia verruculosa* CBS 147.63 genomic DNA as the template.

A haloperoxidase gene segment consisting of approximately 278 codons (834 bp) is amplified from *Curvularia* verruculosa CBS 147.63 as shown in FIG. 7 with the haloperoxidase-specific PCR primers described above. DNA sequence analysis shows that the amplified gene segment encodes a portion of the corresponding *Curvularia verruculosa* haloperoxidase gene. The haloperoxidase gene segment is used to probe a Southern blot of *Curvularia verruculosa* CBS 147.63 genomic DNA.

Example 13

Hybridization analysis of genomic DNA

Total cellular DNA samples prepared from *Curvularia verruculosa* CBS 147.63 described in Example 11 are analyzed by Southern hybridization (Maniatis et al., 1982, *Molecular Cloning, A Laboratory Manual,* Cold Spring Harbor Press, Cold Spring Harbor, N.Y.). Approximately 2–5 μg of DNA is digested with XbaI, BamHI plus HindIII, BamHI plus PstI, or BamHI plus XbaI and fractionated on a 1% agarose gel. The gel is photographed under short wavelength UV light and soaked for 15 minutes in 0.5M NaOH-1.5M NaCl followed by 15 minutes in 1M Tris-HCl pH 8–1.5M NaCl. DNA in the gel is transferred onto a Nytran™ hybridization membrane (Schleicher & Schuell, Keene, N.H.) by capillary blotting in 20 X SSPE (3M sodium chloride-0.2M sodium dibasic phosphate-0.02M disodium EDTA) according to Davis et al. (1980, *Advanced Bacterial Genetics, A Manual for Genetic Engineering,* Cold Spring Harbor Press, Cold Spring Harbor, N.Y.). The DNA is cross-linked onto the membrane using a UV Stratalinker (Stratagene, La Jolla, Calif.), and the membrane is soaked for 2 hours in the following hybridization buffer at 45° C. with gentle agitation: 5 X SSPE, 50% formamide (v/v), 0.3% SDS, and 200 μg/ml denatured and sheared salmon testes DNA. The haloperoxidase gene fragment isolated from the *Curvularia verruculosa* CBS 147.63 PCR-clone as described in Example 2 is radiolabeled and used to probe the Southern blot of *Curvularia verruculosa* CBS 147.63 genomic DNA. Specifically, the gene fragment is radiolabeled by nick translation (Maniatis et al., supra) with α[$^{32}$P] dCTP (Amersham, Arlington Heights, Ill.), denatured by adding NaOH to a final concentration of 0.1M, and added to the hybridization buffer at an activity of approximately 1×10$^6$ cpm per ml of buffer. The mixture is incubated overnight at 45° C. in a shaking water bath. Following incubation, the membranes are washed once in 0.2 X SSPE with 0.1% SDS at 45° C. followed by two washes in 0.2 X SSPE (no SDS) at the same temperature. The membranes are allowed to dry on paper towels for 15 minutes, then wrapped in Saran-Wrap™ and exposed to X-ray film overnight at −70° C. with intensifying screens (Kodak, Rochester, N.Y.).

Figure 8:
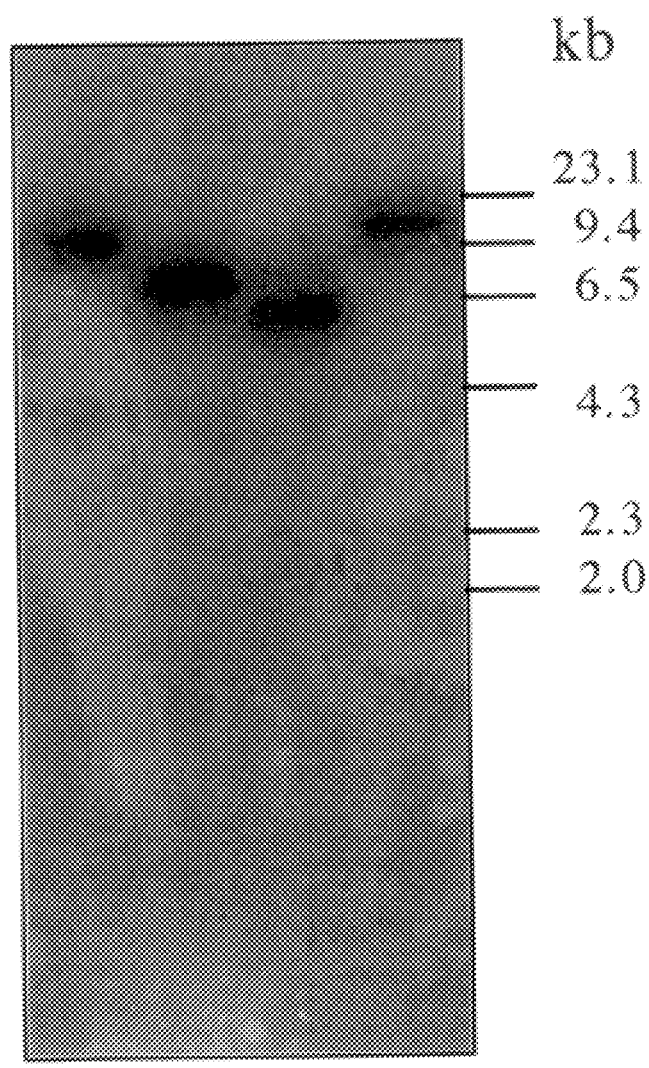
FIG. 8 shows an autoradiogram from a Southern blot of *Curvularia verruculosa* genomic DNA probed with a PCR-derived segment of the haloperoxidase gene.

Analysis of the total cellular DNA samples from *Curvularia verruculosa* CBS 147.63 by Southern blotting under conditions of moderate stringency using the PCR-derived haloperoxidase gene segment probe from *Curvularia verruculosa* CBS 147.63 showed a single hybridization signal (FIG. 8). The single hybridization signal suggests that there is a single copy of the haloperoxidase gene present in the genome of *Curvularia verruculosa* CBS 147.63.

Example 14

DNA libraries and identification of haloperoxidase clones

Figure 9:
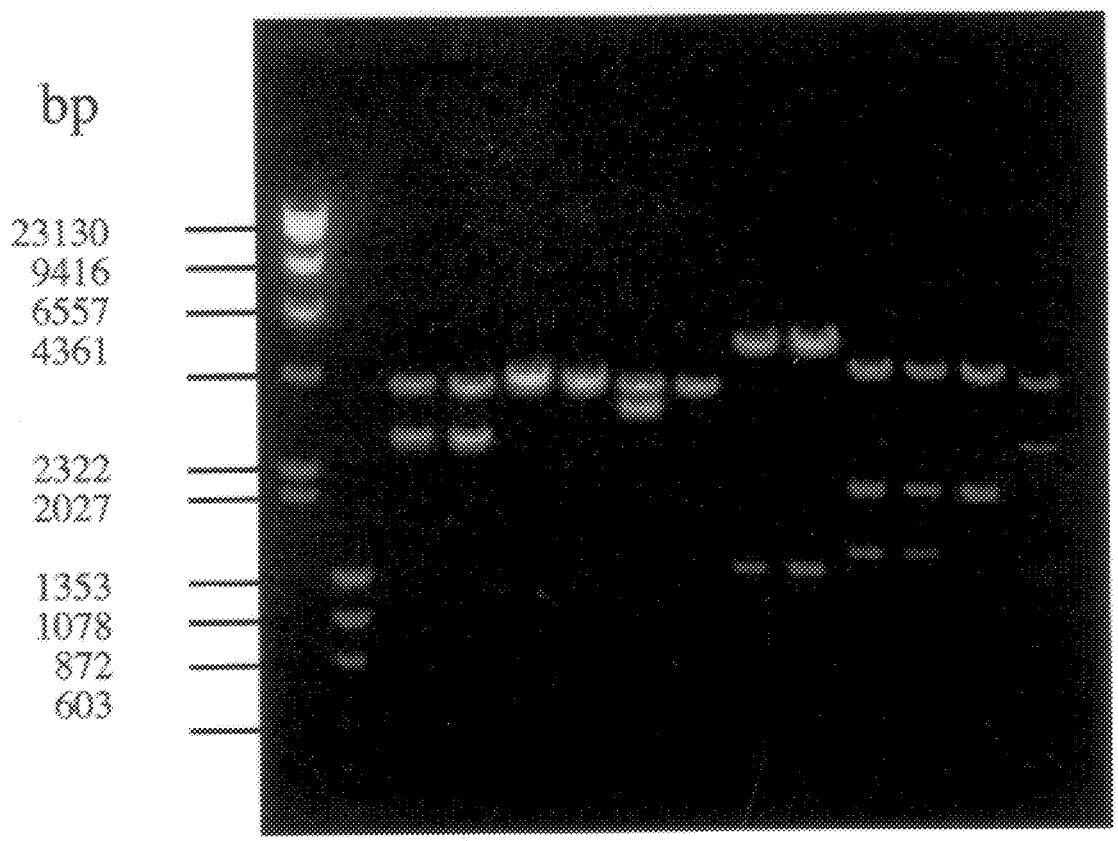
FIG. 9 illustrates an agarose electrophoretic gel of haloperoxidase clones digested with PstI plus HindIII or XhoI plus HindIII.

A genomic DNA library is constructed in the bacteriophage cloning vector λZipLox (Life Technologies, Gaithersburg, Md.). First, total cellular DNA is partially digested with Tsp509I and size-fractionated on 1% agarose gels. DNA fragments migrating in the size range 3–7 kb are excised and eluted from the gel using Prep-a-Gene reagents (BioRad Laboratories, Hercules, Calif.). The eluted DNA fragments are ligated with EcoRI-cleaved and dephosphorylated λZipLox vector arms (Life Technologies, Gaithersburg, Md.), and the ligation mixtures are packaged using commercial packaging extracts (Stratagene, La Jolla, Calif.). The packaged DNA libraries are plated and amplified in *Escherichia coli* Y1090ZL cells (Life Technologies, Gaithersburg, Md.). The unamplified genomic DNA library contained 3.1×10$^5$ pfu/ml (background titers with no DNA are 2.0×10$^4$ pfu/ml). Approximately 60,000 plaques from the library are screened by plaque-hybridization using the haloperoxidase-specific PCR fragment from *Curvularia verruculosa* CBS 147.63 as the probe (Davis et al., 1980, *Advanced Bacterial Genetics, A Manual for Genetic Engineering,* Cold Spring Harbor Press, Cold Spring Harbor, N.Y.). Six plaques, which gave strong hybridization signals with the probe, are purified twice in *E. coli* Y1090ZL cells and the haloperoxidase genes are subsequently excised from the λZipLox vector as pZL1-derivatives (D'Alessio et. al., 1992, *Focus®* 14:76) using in vivo excision by infection of *E. coli* DH10Bzip cells (Life Technologies, Gaithersburg, Md.). Miniprep DNA is prepared from each of these clones and the sizes of the haloperoxidase inserts are determined by agarose gel electrophoresis as shown in FIG. 9. Several of the clones appear to be sibs including two clones designated 4A1 and 4A2 which harbor inserts that comigrate with the plasmid band (ca. 4.3 kb). The haloperoxidase clone 4A (*E. coli* DH10B—pHAP4A.1) is selected for DNA sequence analysis using a Wizard 373 DNA purification kit (Promega, Madison, Wis.).

Example 15

DNA sequence analysis of *Curvularia verruculosa* CBS 147.63 haloperoxidase gene DNA sequencing of the haloperoxidase clone 4A (*E. coli* DH10B—pHAP4A.1) described in Example 14 is performed with an Applied Biosystems Model 373A Automated DNA Sequencer (Applied Biosystems, Inc., Foster City, Calif.) on both strands using a combination of shotgun DNA sequencing and the primer walking technique with dye-terminator chemistry (Giesecke et al., 1992, *Journal of Virol. Methods* 38: 47–60). In addition to the lac-forward and lac-reverse primers, the following oligonucleotide sequencing primers used for gene sequencing are synthesized on an Applied Biosystems Model 394 DNA/RNA Synthesizer according to the manufacturer's instructions:

| Sequencing Primer | Primer Sequence |
|---|---|
| 951337 | dCATGTGGGACGAGCAGGTGCCGTTG (SEQ ID NO: 11) |
| 951338 | dGATAGAAAAGTAGGCATCGTGGATA (SEQ ID NO: 12) |
| 951367 | dCAGAGCTCTGGCAGAGAGAGGCGGTCC (SEQ ID NO: 13) |
| 951368 | dCATTGGGGCTAGGCAGACGGTACGC (SEQ ID NO: 14) |
| 951369 | dGAAGACAGCATCTTGAGAGCAGCTC (SEQ ID NO: 15) |
| 951455 | dCAAGCGTAAGCAGCCAAACTGATCT (SEQ ID NO: 16) |
| 951456 | dGAGATGTACATACGTCAGACCTGGC (SEQ ID NO: 17) |

The nucleotide sequence of the gene encoding the *Curvularia verruculosa* CBS 147.63 haloperoxidase is shown in FIG. 10. Sequence analysis of the cloned insert termed hpxl reveals a large open reading frame of 1800 nt (excluding the stop codon) encoding a protein of 600 amino acids. No introns are present in the gene. The G+C content of this open reading frame is 57%.

The deduced amino acid sequence of the *Curvularia verruculosa* CBS 147.63 haloperoxidase as shown in FIG. 10 indicates that the calculated molecular weight of the primary translation product is 66,593 which is consistent with the estimate of 68 kDa based on the mobility of the purified protein on SDS-PAGE and the amino acid sequences of peptides derived from the purified haloperoxidase described above.

The deduced amino acid sequence predicts the presence of only two Cys residues in the *Curvularia verruculosa* haloperoxidase which are likely present as free thiols in the active enzyme which is consistent with the haloperoxidase from *Curvularia inaequalis* (Simons et al., 1995, *European Journal of Biochemistry* 229:566–574). There are three potential sites for N-glycosylation. Monosaccharide composition analysis of the *Curvularia verruculosa* haloperoxidase, as described in Example 8, indicates that the haloperoxidase is glycosylated with 3 pmol of galactose, 16 pmol of glucose, and 29 pmol of mannose per pmol of haloperoxidase. However, since the observed molecular weight of the *Curvularia verruculosa* haloperoxidase (68 kDa) is very close to the calculated size (MW=66,573), the extent of glycosylation is likely very small. Furthermore, the absence of glucosamine in this analysis suggests that the carbohydrate moieties are O-linked. This result is in contrast to the haloperoxidase from *Curvularia inaequalis* which is reportedly unglycosylated (Simons et al., 1995, *European Journal of Biochemistry* 229:566–574).

The deduced amino acid sequence of the *Curvularia verruculosa* haloperoxidase is 90.9% identical to that of the *Curvularia inaequalis* haloperoxidase as shown in FIG. 11. Interestingly, the *Curvularia inaequalis* haloperoxidase is nine residues longer than the *Curvularia verruculosa* haloperoxidase and are present as two clusters, one near the N-terminus and the other at the C-terminus of the *Curvularia inaequalis* haloperoxidase.

Example 16

Production of *Curvularia verrculosa* CBS 444.70 haloperoxidase

A seed culture of *Curvularia verruculosa* CBS 444.70 is produced in a 500 ml shake flask containing 100 ml of medium with the following composition:

| | |
|---|---|
| Corn steep liquor (dried) | 1.2 g |
| Glucose | 2.4 g |
| $CaCO_3$ | 0.5 g |
| Soy Oil | 0.5 ml |

The pH is adjusted to 5.5 before autoclaving.

After 3 days growth at 26° C. and 250 rpm, a 10 liter lab fermentor is inoculated with the seed culture described above. The composition of the medium in the fermentor is:

| | |
|---|---|
| Yeast extract (Difco 0127) | 8 g/l |
| $K_2HPO_4$ (Merck 5101) | 2 g/l |
| $MgSO_4.7H_2O$ (Merck 5886) | 1 g/l |
| Dextrose (Roquelle 101-0441) | 30 g/l |
| $Na_3VO_4$ | 1 mg/l |

The pH was not adjusted but measured to 6.2. The fermentation takes place at 26° C., 550 rpm, for 7 days.

Example 17

Purification of *Curvularia verruculosa* CBS 444.70 haloperoxidase

The culture broth prepared as described in Example 16 is centrifuged, filtered (GF/F Whatman), and further concentrated approximately 80 fold on a Filtron-apparatus (membrane cut-off: 10000 Da), and further concentrated in an Amicon cell (PM 10). The concentrated broth is loaded onto a Q-Sepharose FF-column (100 ml, XK26, Pharmacia) previously equilibrated in 10 mM potassium phosphate pH 7 (buffer A) at a flow rate of 5 ml/min. The column is washed with 200 ml of 10 mM potassium phosphate pH 7 and then eluted with a gradient from 0→1M NaCl in the same buffer over 200 minutes. Fractions of 10 ml are collected and pooled according to the presence of haloperoxidase activity as described in Example 2. Fractions 36–45 are pooled and concentrated on an Amicon-cell (PM 10) and Centricon-10. Samples of 1.5 ml of the concentrate are loaded onto a HiLoad Superdex 75-column (Pharmacia) equilibrated with 50 mM sodium phosphate pH 7.1, and the haloperoxidase is eluted at a flow rate of 1 ml/min. Fractions of 1.5 ml are collected and assayed for haloperoxidase activity as described in Example 2. Fractions containing haloperoxidase activity are pooled.

Example 18

Antibacterial activity of *Curvularia verruculosa* CBS 444.70 haloperoxidase The antibacterial activity of the *Curvularia verruculosa* CBS 444.70 haloperoxidase prepared as described in Example 17 is tested against the following four different non-pathogenic bacteria:

Gram-negative bacteria

*Pseudomonas flourescens* (ATCC 13525)

*Vibrio alginolyticus* (ATCC 17749)

Gram-positive bacteria

*Listeria innocua* (ATCC 33090)

*Micrococcus luteus* (ATCC 10240).

The test organisms are cultivated in TY medium (adjusted to pH 7.3 with potassium hydroxide) comprising the following components:

| | |
|---|---|
| Trypticase | 20 g/liter |
| Yeast Extract | 5 g/liter |
| $FeCl_2.4H_2O$ | 6 mg/liter |
| $MnCl_2.7H_2O$ | 1 mg/liter |
| $MgSO_4.7H_2O$ | 15 mg/liter |

Antibacterial Activity

The test organisms ($10^7$–$10^8$ CFU/ml where CFU=colony forming units) in TY-media are incubated at 30° C. with one of the following solutions (haloperoxidase solutions are 0.2$\mu$ membrane filtered):

(1) 10 ppm benzalkoniumchloride;

(2) a glucose oxidase obtained *Aspergillus niger* having an activity of 0.2 GODU/ml (Sigma)+10 mM glucose;

(3) a glucose oxidase obtained *Aspergillus niger* having an activity of 0.2 GODU/ml (Sigma)+10 mM glucose+1 mM SCN-;

(4) a glucose oxidase obtained *Aspergillus niger* having an activity of 0.2 GODU/ml (Sigma)+10 mM glucose+ 0.1 HU/ml *C. verruculosa* haloperoxidase; and (5) a glucose oxidase obtained *Aspergillus niger* having an activity of 0.2 GODU/ml (Sigma)+10 mM glucose+1 mM SCN-+0.1 HU/ml *C. verruculosa* haloperoxidase.

Glucose oxidase activity is determined by oxidation of D-glucose by oxygen to gluconic acid and hydrogen peroxide. The hydrogen peroxide produced thereby is reduced by peroxidase and 2,2'-azinobis(3-ethylbenzothiazoline-6-sulfonate) to water. The greenish-blue color produced is measured at 418 nm. The analytical conditions are 0.1M sodium acetate, 90 mM β-D-glucose, pH 5.6, 30° C., and 20 minutes reaction. One glucose oxidase unit (GODU) is defined as the amount of glucose oxidase that catalyzes the conversion of 1 μmole of hydrogen peroxide per minute under these conditions.

The growth inhibition of Listeria and Micrococcus is followed at 30° C. and the turbidity is measured at 490 nm.

The results presented in Table 3 demonstrate that the growth of Listeria or Micrococccus is inhibited after treatment with solution 5, although the growth of Micrococcus was sensitive to solution 2.

TABLE 3

Growth of the gram-positive bacteria expressed in % relative to the control; turbidity increase at 490 nm after 24 hours of incubation is measured

| Conditions | Listeria | Micrococcus |
| --- | --- | --- |
| Control | 100 | 100 |
| solution 1 | 0 | 0 |
| solution 2 | 143 | 2 |
| solution 3 | 98 | 4 |
| solution 4 | 304 | 130 |
| solution 5 | 0 | 1 |

Lower cell numbers of the test organisms ($10^5$–$10^6$ CFU/ml) are incubated with the above solutions in 50 mM sodium phosphate pH 7 buffer for 1 hour and plated onto TY-agar. When solution 5 is used, the gram-negative bacteria (Pseudomonas and Vibrio) are severely affected while the gram-positive bacteria survive under the given conditions as shown in Table 4. The survival of the gram-positive bacteria may be due to the limited incubation time (1 hour).

TABLE 4

Antibacterial activity of purified haloperoxidase as % survival based on CFU counts

| Conditions | Pseudomonas | Vibrio | Listeria |
| --- | --- | --- | --- |
| Control | 100 | 100 | 100 |
| solution 1 | 0 | 3 | 0 |
| solution 3 | 99 | 87 | 85 |
| solution 4 | 62 | 6 | 101 |
| solution 5 | 2 | 3 | 55 |

Example 19

Figure 12:
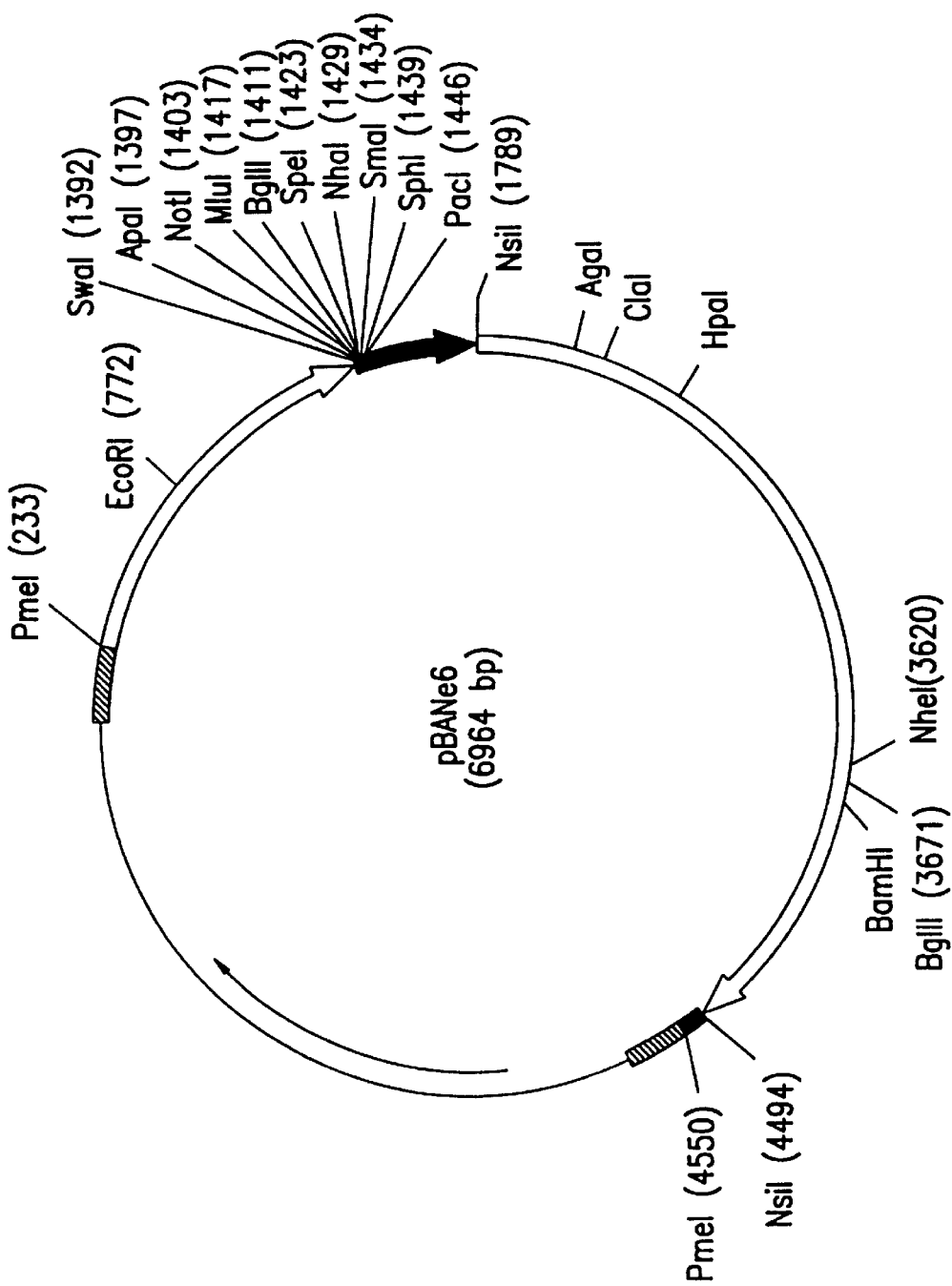
FIG. 12 shows a restriction map of pBANe6.

Construction of a *Curvularia verruculosa* CBS 147.63 Haloperoxidase (hpxI) *Aspergillus oryzae* expression plasmid The coding region of the *Curvularia verruculosa* CBS 147.63 haloperoxidase gene (hpx) is amplified and the resulting fragment is cloned into pBANe6 for expression in *Aspergillus oryzae*. pBANe6 provides the TAKA/NA2-tpi promoter, the AMG 3' terminator, and the amdS selectable marker gene (FIG. 12). Specifically, the fragment is amplified by PCR using a sense primer (aHaP1) designed to the first in-frame ATG and extending 20 bp downstream and an antisense primer (aHaP1A) designed to a region 14 bp downstream of the transcriptional stop codon and extending 19 bp downstream. To facilitate the cloning of the amplified fragment the sense and antisense primers contain a SwaI and a PacI restriction site, respectively. The oligonucleotide primers shown below are synthesized using an ABI Model 394 DNA/RNA Synthesizer (Applied Biosystems, Inc., Foster City, Calif.).

SwaI aHaP1 5'GCATATTTAAATGATGGGGTCCGTTA-CACCAAT (SEQ ID NO: 18)

PacI aHaP1A 5'ATATTAATTAATCACTGGTAAACTCTGCCG (SEQ ID NO: 19)

The 50 μl PCR solution (10 mM Tris-HCl pH 8.3, 50 mM KCl, 1.5 mM $MgCl_2$, 0.01% w/v gelatin) contains approximately 200 ng of hpx1 DNA, 200 μM each of dATP, dCTP, dGTP, and dTTP, and 50 pmol of each PCR primer described above. Five units of PWO polymerase (Boehringer Mannheim, Indianapolis, Ind.) are added and the reaction is incubated at 95° C. for 3 minutes and cooled to 80° C. The reaction is then cycled 30 times, each cycle at 95° C. for 30 seconds, 57° C. for 1 minute, and 72° C. for 1 minute, in a Perkin-Elmer 9600 Thermal Cycler. Following the last cycle, the reaction incubated for 5 minutes at 72° C.

Figure 13:
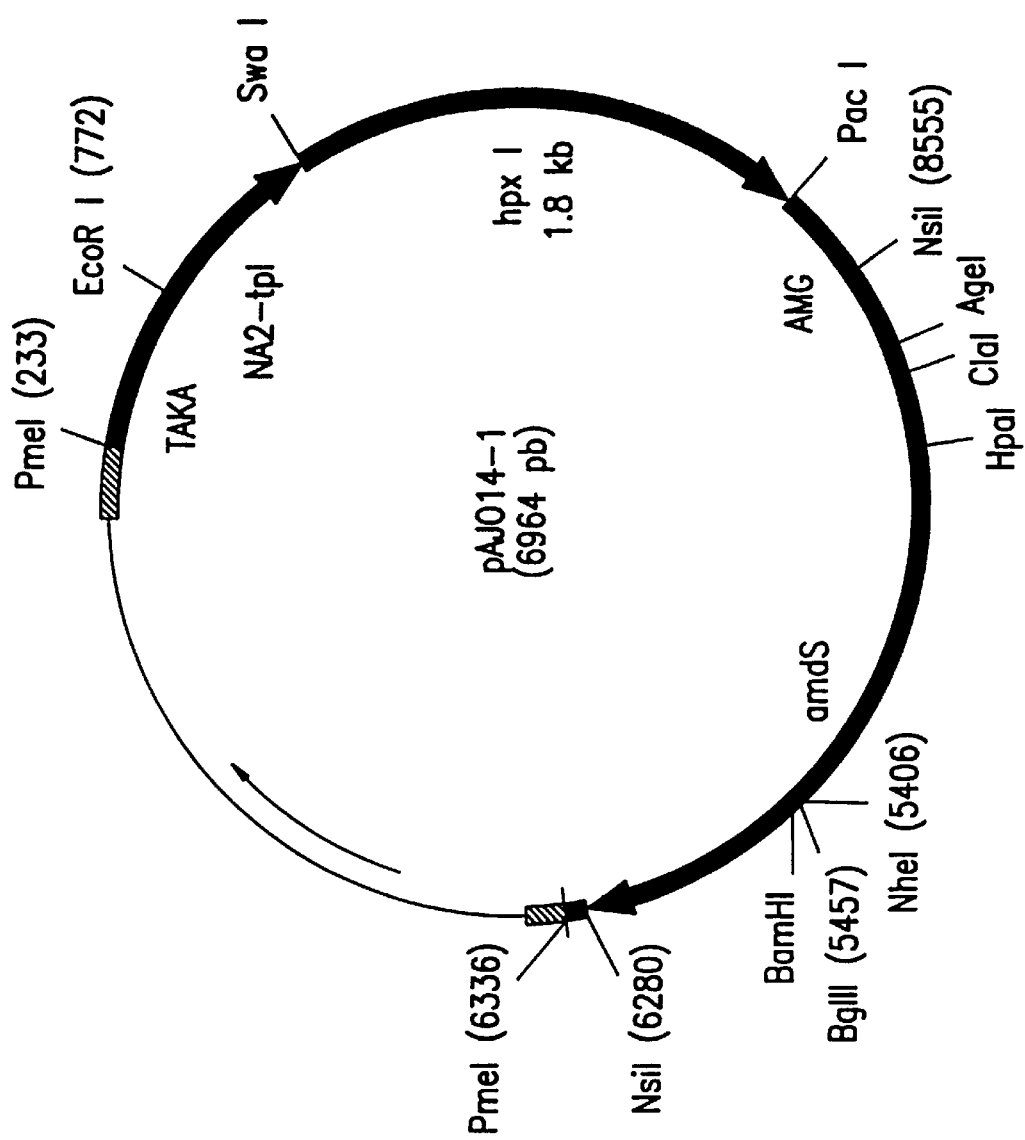
FIG. 13 shows a restriction map of pAJO14-1.

A predicted 1.8 kb fragment is isolated by digestion with SwaI and PacI and is cloned into pBANe6 digested with the same restriction endonucleases to create pAJ014-1 (FIG. 13). To verify the fidelity of the cloned PCR fragment, the fragment is sequenced according to the method of Hattori and Sakaki (1986, *Analytical Biochemistry* 152:232–237) using an automated Applied Biosystems Model 373A Sequencer (Applied Biosystems, Inc., Foster City, Calif.).

Sequencing of the cloned hpxI amplified insert of pAJ014-1 confirms that there are no differences in the sequence described in SEQ ID NO:1.

Example 20

Transformation of *Aspergillus oryzae* strain JaL142 with

*Aspergillus oryzae* strain JaL142 is transformed with pAJ014-1 according to the following procedure. The transformation is conducted with protoplasts at a concentration of $2 \times 10^7$ protoplasts per ml. One hundred μl of protoplasts are incubated at 34° C. with 10 μg DNA and 200 μl of 60% PEG 4000-10 mM HEPES-10 mM $CaCl_2$ solution for 30 minutes. Three ml of SPTC (40% PEG 4000, 0.8M sorbitol, 0.05M Tris pH 8.0, 0.05M $CaCl_2$) are added and the protoplasts are plated directly onto COVE transformation plates (342.3 g of sucrose, 25 g of Noble agar, 10 ml of 1M acetamide, 20 ml of COVE salts solution, and 10 ml of 3M CsCl per liter) for amdS transformations. The COVE salts solution (50X) is comprised of 26 g of KCl, 26 g of $MgSO_4$-$7H_2O$, 76 g of $KH_2PO_4$, and 50 ml of COVE trace metals solution. The COVE trace metals solution is comprised of 0.04 g of $NaB_4O_7$-$10H_2O$, 0.04 g of $CuSO_4$-$5H_2O$, 0.70 g of $FeSO_4$-$H_2O$, 0.80 g of $Na_2MoO_2$-$2H_2O$, and 10 g of $ZnSO_4$ per liter. Plates are incubated 5–7 days at 34° C. The transformants are transferred to plates of the same medium and incubated 3–5 days at 34° C. The transformants are then purified by streaking spores and picking isolated colonies using the same plates under the same conditions.

Example 21

Expression of *Curvularia verruculosa* CBS 147.63 haloperoxidase in *Aspergillus oryzae*

Twenty-four transformants from Example 20 are each inoculated into 1 ml of ¼ strength MY50N medium supplemented with 1 mM $V_2O_5$ in a 24-well plate. MY50N medium is comprised of per liter 62.5 g nutriose, 2 g $MgSO_4$-$7H_2O$, 2 g $KH_2PO_4$, 4 g citric acid, 8 g yeast extract, 2 g urea, 0.1 g $CaCl_2$, and 0.5 ml trace metals. The trace metals solution is comprised of 22 g of $ZnSO_4$-$7H_2O$, 11 g of $H_3BO_3$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$ per liter. The cultures are grown for 5 days at 34° C. with shaking at 150 rpm and then are assayed for haloperoxidase activity using the procedure described in Example 2 except the assay buffer also contains 1.25 mM $V_2O_5$ for activation of the enzyme. Assays are initiated by addition of 10 μl of 0.3% $H_2O_2$ and absorption at 600 nm is monitored as a function of time during incubation at 30° C. Activity is expressed as the change in absorbance at 600 nm per minute per ml ($mOD_{600}$/minute-ml).

The twenty-four transformants all have haloperoxidase detectable activity, ranging from 250 to 8,390 $mOD_{600}$/minute-ml. SDS-PAGE of samples from the 24-well plate readily demonstrates the presence of a 66 kDa band corresponding to the haloperoxidase whose abundance correlated well with the assay results.

The best eight transformants are then spore purified two times and inoculated into 125 ml baffled shake flasks containing 25 ml of MY50N medium supplemented with 1 mM $V_2O_5$, and grown for 5 days at 34° C. with shaking at 250 rpm. These cultures are assayed after 5 days growth, and the best isolate, HaP14, is run in a fermenter.

Figure 14:
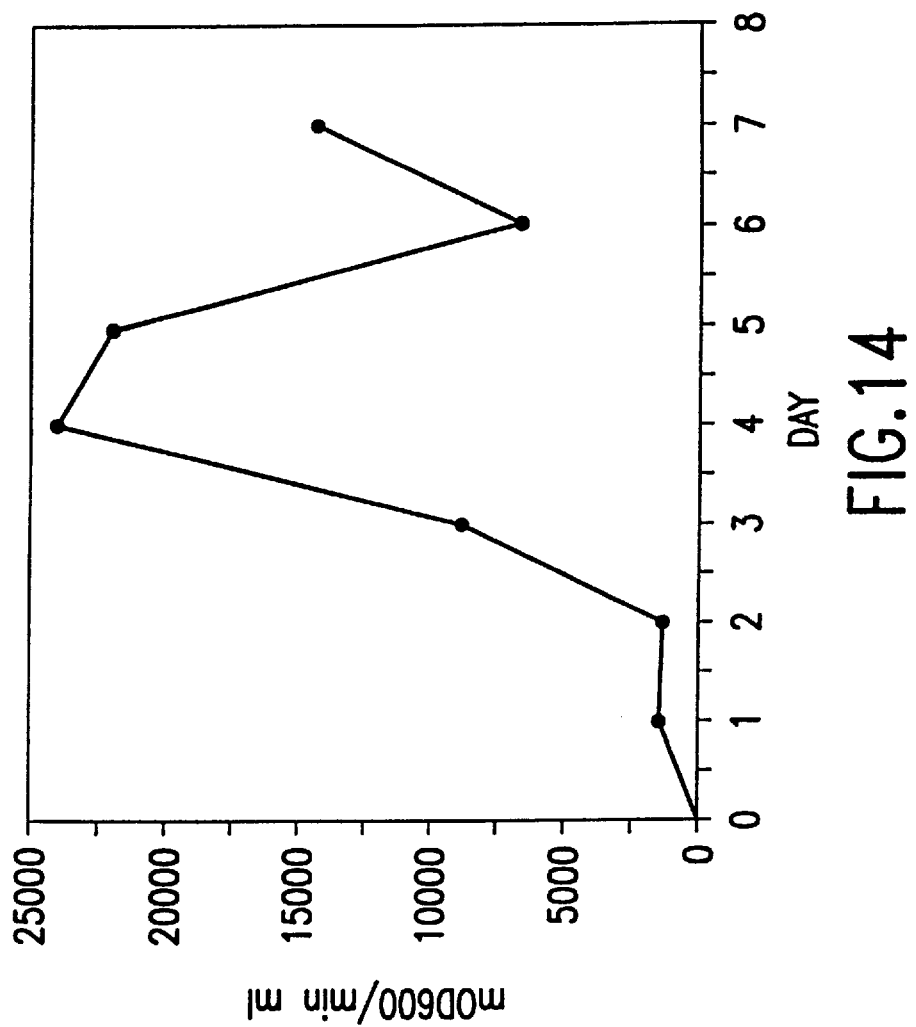
FIG. 14 shows the time course of haloperoxidase production during fermentation.

HaP14 is fermented in a tank medium comprised of 30 g of Nutriose, 10 g of yeast extract, 2 g of $MgSO_4$-$7H_2O$, 2 g of $K_2SO_4$, 2 g of citric acid, 3 g of $CaCl_2$, and 0.5 ml of trace metals solution (described above) per liter and fed during the course of the fermentation with a medium comprised of 400 g of Nutriose, 20 g of urea, and 1 g of citric acid per liter. The fermentation is allowed to proceed for 7 days at 34° C., pH 7.2, at which time proximately 1.2 liters of broth is harvested. Assays performed on broth samples from days 1 to 7 of the fermentation suggest that haloperoxidase production peaked at day 4 and lined thereafter, although production appeared to recover slightly at day 7 (FIG. 14).

DEPOSIT OF MICROORGANISMS

The following strain has been deposited according to the Budapest Treaty in the Agricultural Research Service Patent Culture Collection (NRRL), Northern Regional Research Laboratory, 1815 University Street, Peoria, Ill. 61604, USA.

| Strain | Accession Number | Deposit Date |
|---|---|---|
| E. coli DH10B (pHAP4A.1) | NRRL B-21519 | January 18, 1996 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosures of which are incorporated by reference in their entireties.

What is claimed is:

1. An isolated haloperoxidase obtained from a *Curvularia verruculosa* strain.

2. A haloperoxidase according to claim 1 which is obtained from *Curvularia verruculosa* CBS 147.63 or a mutant strain thereof.

3. A haloperoxidase according to claim 1 which is obtained from *Curvularia verruculosa* CBS 444.70 or a mutant strain thereof.

4. A haloperoxidase according to claim 1 which retains at least 50% activity after one hour incubation at pH 7.0 and 60° C. in the presence of 0.1% $H_2O_2$.

5. A haloperoxidase according to claim 1 which retains at least 75% activity after one hour incubation at pH 7.0 and 60° C. in the presence of 0.1% $H_2O_2$.

6. A haloperoxidase according to claim 1 which retains at least 50% activity at 30° C. over a pH range of between about 4 and about 11.

7. A haloperoxidase according to claim 1 which retains at least 80% activity at 30° C. over a pH range of between about 4 and about 11.

8. A haloperoxidase according to claim 1 which has a temperature optimum in the range of 50°–70° C.

9. A haloperoxidase according to claim 1 which has a temperature optimum in the range of 55°–65° C.

10. A haloperoxidase according to claim 9 which has a temperature optimum of about 60° C. at pH 5.5.

11. A haloperoxidase according to claim 1 which has a pH optimum in the range of about 5.25 to about 6.25.

12. A haloperoxidase according to claim 11 which has a pH optimum of about 5.75 at 30° C.

13. A haloperoxidase according to claim 1 which prefers $Br^-$ over $Cl^-$ as a substrate.

14. A haloperoxidase according to claim 1 which contains the partial peptide sequence set forth in SEQ ID NO:3.

15. A haloperoxidase according to claim 1 which contains the partial peptide sequence set forth in SEQ ID NO:4.

16. A haloperoxidase according to claim 1 which contains the partial peptide sequence set forth in SEQ. ID NO:5.

17. A haloperoxidase according to claim 1 which contains the partial peptide sequence set forth in SEQ ID NO:6.

18. A haloperoxidase according to claim 1 which contains the partial peptide sequence set forth in SEQ ID NO:7.

19. A haloperoxidase according to claim 1 which contains the partial peptide sequence set forth in SEQ ID NO:8.

20. A haloperoxidase according to claim 1 which contains the partial peptide sequence set forth in SEQ ID NO:9.

21. A haloperoxidase according to claim 1 which contains the partial peptide sequence set forth in SEQ ID NO:10.

22. A haloperoxidase according to claim 1 which has an amino acid sequence set forth in SEQ ID NO:2.

23. An isolated haloperoxidase which is encoded by the coding region of the nucleic acid sequence contained in the plasmid pHAP4A.1 of *E. coli* DH10B, NRRL B-21519.

24. A method for producing the haloperoxidase of claim 1 comprising (a) fermenting a *Curvularia verruculosa* strain to produce a supernatant comprising the haloperoxidase; and (b) recovering the haloperoxidase.

* * * * *

UNITED STATES PATENT AND TRADEMARK OFFICE
CERTIFICATE OF CORRECTION

PATENT NO. : 5,866,393
DATED : February 2, 1999
INVENTOR(S) : Fuglsang et al.

It is certified that error appears in the above-identified patent and that said Letters Patent is hereby corrected as shown below:

Col. 5, line 44: after "e.g.", insert --,--

Col. 5, line 64: delete "(amyQ)" and insert --(amyM)--

Col. 6, line 63: delete "stearothennophilus" and insert --stearothermophilus--

Signed and Sealed this

Thirtieth Day of November, 1999

Attest:

Q. TODD DICKINSON

*Attesting Officer*  *Acting Commissioner of Patents and Trademarks*